United States Patent [19]
Mochizuki et al.

[11] Patent Number: 5,643,920
[45] Date of Patent: Jul. 1, 1997

[54] TRICYCLIC COMPOUND HAVING ANTI-ALLERGIC ACTIVITIES

[75] Inventors: Hidenori Mochizuki; Kazuo Kato; Ichiro Yamamoto; Kiyoshi Mizuguchi, all of Tokyo, Japan

[73] Assignee: Mochida Pharmaceutical Co., Ltd., Tokyo, Japan

[21] Appl. No.: 325,339

[22] PCT Filed: Apr. 27, 1993

[86] PCT No.: PCT/JP93/00549

§ 371 Date: Oct. 27, 1994

§ 102(e) Date: Oct. 27, 1994

[87] PCT Pub. No.: WO93/22313

PCT Pub. Date: Nov. 11, 1993

[30] Foreign Application Priority Data

Apr. 27, 1992 [JP] Japan .................. 4-134189

[51] Int. Cl.$^6$ .................. A61K 31/44; C07D 455/03; C07D 221/06
[52] U.S. Cl. .................. 514/294; 546/79; 546/94
[58] Field of Search .................. 546/79, 94; 514/294

[56] References Cited

U.S. PATENT DOCUMENTS 3,200,123  8/1965  Richardson, Jr. et al. .................. 546/84
5,151,431  9/1992  Inaba et al. .................. 514/292

FOREIGN PATENT DOCUMENTS 0157346  10/1985  European Pat. Off. .
0436245   7/1991  European Pat. Off. .
3-27382   2/1991  Japan .
4-145083  5/1992  Japan .

OTHER PUBLICATIONS

Meth–Cohn et al, Journal of the Chemical Society, pp. 2609–2614 (1964).
Richardson, Jr. et al, J. of Organic Chem., 25:1138–1147 (Jul. 1960).
Kakehi et al, Chem. Pharm. Bull., vol. 34, No. 6, pp. 2435–2443 (1986).
Peet et al, J. Med. Chem., 28:298–302 (1985).
Noguchi et al, Heterocycles, vol. 31, No. 3, pp. 563–568 (1990).
Noguchi et al, Bull. Chem. Soc. Jpn., 61:423–429 (1988).
Cardellini et al, J. Org. Chem., 47:688–692 (1982).
Geneste et al, Eur. J. Med. Chem.—Chimica Therapeutica, vol. 12, No. 5, pp. 471–476 (1977).
Tao et al, Steroids, vol. 27, No. 2, pp. 205–210 (Feb. 1976).

*Primary Examiner*—Alan L. Rotman
*Attorney, Agent, or Firm*—Birch, Stewart, Kolasch & Birch, LLP

[57] ABSTRACT

A nitrogen-containing tricyclic compound represented by formula (I):

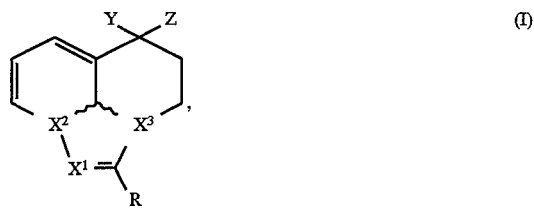

a salt thereof, or a solvate of said compound or said salt, wherein R represents phenyl or naphthyl group which is unsubstituted or substituted at one to five sites with a group such as a halogen atom; a straight chain or branched alkyl group containing 1 to 10 carbon atoms which is unsubstituted or substituted with one or more halogen atoms; or the like; Y represents hydrogen atom; and Z represents a group such as hydrogen atom, hydroxyl group, or the like; or Y and Z together represent a group such as hydrazono group, hydroxyimino group, or the like which is unsubstituted or substituted with a particular group; and $X^1$–$X^2$–C–$X^3$ represents CH—N—C=C or N—C=C—N; provided that when $X^1$–$X^2$–C–$X^3$ represents N—C=C—N, Y and Z does not together represent hydroxyimino group or oxygen atom; is capable of inhibiting the production of IgE antibody, and therefore, is useful as a prophylactic and/or therapeutic agent for allergic diseases.

11 Claims, No Drawings

TRICYCLIC COMPOUND HAVING ANTI-ALLERGIC ACTIVITIES

CROSS-REFERENCE

This application is a 371 or PCT/JP 93/00549 filed Apr. 27, 1993.

FIELD OF THE INVENTION

This invention relates to a prophylactic and/or therapeutic agent for allergic diseases wherein immunoglobulin E antibody (hereinafter referred to as IgE antibody) is involved, for example, some types of bronchial asthma, conjunctivitis, rhinitis, dermatis, and hypersensitivity.

BACKGROUND ART

Allergic reactions involved in allergic diseases, for example, some types of bronchial asthma, conjunctivitis, rhinitis, dermatis, and hypersensitivity are caused by the release of various chemical mediators such as histamine, prostaglandin, leukotriene, thromboxane, and platelet activating factor from mast cells or basophils upon binding of the particular antigen with IgE antibody on the surface of such cells. Various symptoms are induced by such allergic reactions, and nosotropic therapies are most commonly employed to relieve such symptoms. Etiotropic therapies are also popular that employ compounds such as sodium cromoglicate, tranilast, ketotifen, and azelastine, that are capable of inhibiting the release of chemical mediators among the series of allergic reactions. However, compounds that are capable of blocking the stage of reactions preceding the release of chemical mediators are scarcely known, and the development of such compounds useful for pharmaceutical composition is sincerely awaited. In view of such conditions, a compound capable of inhibiting the production of IgE antibody, that is responsible for various allergic diseases as mentioned above, would be highly useful as a therapeutic agent to enable the more etiotropic treatment of such diseases.

Prior arts relating to the compound of the present invention are hereinafter described.

U.S. Pat. No. 3,200,123 discloses 2-substituted-5,6-dihydroimidazo[ij]quinoline derivatives having an inflammatory activity without any pharmacological data. intensity and detailed mechanism of such activity of the individual compound are unknown. In Journal of Organic Chemistry, 25, 1138–1147, 1960, the inventors of the U.S. Pat. No. 3,200,123 reported that only some compounds among the above-mentioned dihydroimidazo[ij]quinoline derivatives proved effective in animals with dextran sulfate-induced edema. Both prior art documents fail to indicate anti-allergic activities, in particular, the activity to suppress IgE antibody production.

Some 1-substituted-8,9-dihydro-7H-pyrrolo[3,2,1-ij] quinoline derivatives are reported in Bulletin of the Chemical Society of Japan, 61, 423–429, 1988. These compounds are intermediate products in the synthesis of 3-phenyl-4H-benzo[hi]pyrrolo[2,1,5-cd]indolizine-4-one compounds, whose electronic features are of engineering interest. This document does not at all disclose pharmacological activities.

Chemical and Pharmaceutical Bulletin, 34, 2435–2442, 1986 discloses tricyclic and tetracyclic indolizine compounds having anti-allergic activities. However, these compounds significantly differ from the compounds of the present invention in their types of substituents and sites of the substitution. Further this document also fails to disclose specific biological activities.

Journal of Medicinal Chemistry, 28, 298–302, 1985 discloses that PCA reaction is suppressed in rat by a 6-oxo-6H-imidazo[4,5,1-ij]quinoline-4-carboxylic acid derivative. However, it is also disclosed in this document that this compound simultaneously proved to be toxic to kidney. The compound of this document differs from the compounds of the present invention in its structure. This document also fails to refer to the activity of inhibiting the IgE antibody production.

There are known many other compounds that have the nitrogen-containing tricyclic skeleton identical with that of the compound of the present invention. However, no report has so far indicated the anti-allergic activity.

Among a variety of therapeutic agents for allergic diseases that have been developed, compounds disclosed in Japanese Patent Application Laid-Open (Kokai) Nos. 59(1984)-167564, 1(1989)-149784, 2(1990)-25906, and the like are known to have been developed from the view point of inhibiting the IgE antibody production. In the specification of some of these compounds, there are disclosures that some compounds inhibited the production of IgE antibody in some model animals. However, the degrees of the inhibitions are not quite sufficient, and none of such compounds have so far been used as a commercial pharmaceutical agent, yet.

SUMMARY OF THE INVENTION

It has been recognized in animal experiments and in clinical practice that the production of IgE antibody is induced by sensitization with particular types of antigens, and the thus induced IgE production is likely to constitute for a considerably long period. Accordingly, a therapeutic agent for allergic diseases that attempts to inhibit the IgE antibody production would be required to inhibit not only the IgE antibody production during immune response induction phase but also the subsequent IgE antibody production that continues after the immune response induction phase.

Under such conditions, there has been a demand for a therapeutic agent for allergic diseases which is capable of sufficiently inhibiting the IgE antibody production for a considerably long period, and which is highly active and safe upon administration to human.

In view of such above situation, the inventors of the present invention have for many years searched for a compound that is capable of sufficiently inhibiting the continuous production of the IgE antibody which is responsible for the allergic diseases. After such investigation, the inventors of the present invention found that the nitrogen-containing tricyclic compound and the salt thereof of the present invention are capable of sufficiently inhibiting the IgE antibody production for a prolonged period. The present invention has been completed on such a finding.

According to the present invention, there is provided a nitrogen-containing tricyclic compound represented by formula (I):

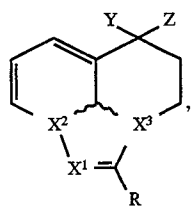

a salt thereof, or a solvate of said compound or said salt, wherein

R represents phenyl or naphthyl group which is unsubstituted or substituted at one to five sites with a group optionally selected from a halogen atom; a straight chain or branched alkyl group containing 1 to 10 carbon atoms which is unsubstituted or substituted with one or more halogen atoms; cyano group; carboxyl group; an alkoxycarbonyl group containing 1 to 4 carbon atoms; hydroxyl group; a straight chain or branched alkoxyl group containing 1 to 4 carbon atoms which is unsubstituted or substituted with one or more halogen atoms; phenoxy group; tetrazolyl group; amino group which is unsubstituted or substituted at least at one site with a straight chain or branched alkyl group containing 1 to 4 carbon atoms; and nitro group;

Y represents hydrogen atom; and

Z represents hydrogen atom; hydroxyl group; acetoxy group; amino group which is unsubstituted or substituted with methylthiopropanoyl group, an alkyl group containing 1 to 4 carbon atoms, an aminoalkyl group containing 1 to 4 carbon atoms, hydroxyethylaminoethyl group, an alkoxyoxalyl group containing 1 to 4 carbon atoms, or an alkylidene group containing 2 to 6 carbon atoms; nitro group; or an alkyl group containing 1 to 4 carbon atoms substituted with amino group; or Y and Z together represent hydrazono group which is unsubstituted or substituted at least at one site with an alkyl group containing 1 to 4 carbon atoms, an alkylidene group containing 2 to 6 carbon atoms, an alkoxycarbonyl group containing 1 to 4 carbon atoms, phenyl group, tosyl group, formyl group, carbamoyl group, amidino group, imidazolidinyl group, pyridyl group, or methoxyphenylethylpiperidinylcarbonyl group; hydroxyimino group which is unsubstituted or substituted with an alkyl group containing 1 to 4 carbon atoms which is unsubstituted or substituted with an alkoxycarbonyl group containing 1 to 4 carbon atoms or carboxyl group, tosyl group, or tetrazolylmethyl group; imino group substituted with an unsubstituted or substituted heteromonocyclic group; methylene group which is unsubstituted or substituted with cyano group or an aminoalkyl group containing 1 to 4 carbon atoms; or oxygen atom; and $X^1$-$X^2$-C-$X^3$ represents CH—N—C=C or N—C=C—N; provided that when $X^1$-$X^2$-C-$X^3$ represents N—C=C—N, Y and Z do not together represent hydroxyimino group or oxygen atom. According to the present invention, there are also provided a process for producing such a compound, as well as a therapeutic agent for allergic diseases characterized by the inclusion of such a compound.

When Y and Z together represent hydrazono group which is unsubstituted or substituted at least at one site with an alkyl group containing 1 to 4 carbon atoms, an alkylidene group containing 2 to 6 carbon atoms, an alkoxycarbonyl group containing 1 to 4 carbon atoms, phenyl group, tosyl group, formyl group, carbamoyl group, amidino group, imidazolidinyl group, pyridyl group, or alkoxyphenylalkylpiperidinylcarbonyl group; hydroxyimino group which is unsubstituted or substituted with an alkyl group containing 1 to 4 carbon atoms which is unsubstituted or substituted with an alkoxycarbonyl group or carboxyl group, tosyl group, or tetrazolylmethyl group; imino group substituted with an unsubstituted or substituted heteromonocyclic group; or methylene group which is substituted with cyano group or an aminoalkyl group in the compound of the formula (I), a syn-isomer, an anti-isomer, and mixtures thereof may be present for each of the N—N bond in the hydrazono group, the N—O bond in the hydroxyimino group, the bond between the heteromonocyclic group and nitrogen atom of the imino group, and the bond between the cyano or the aminoalkyl group and the methylene group. It should be understood that all of such isomers and the mixtures thereof are within the scope of the present invention.

Furthermore, when Y represents hydrogen atom and Z represents a group other than hydrogen atom in the compound of the formula (I), two optical isomers are present. It should be understood that both optical isomers and the mixtures thereof are also within the scope of the present invention.

The nitrogen-containing tricyclic compound of the present invention is capable of highly inhibiting the production of IgE antibody for a prolonged period, and simultaneously, has an activity to directly suppress the release of histamine, which is known to be one of major causes for constriction of bronchial smooth muscle. Therefore, the therapeutic agent for allergic diseases of the present invention may be used for preventing, relieving, and curing the allergic disease that are mediated by IgE antibody.

In the compounds of the present invention, R in formula (I) may preferably be phenyl or naphthyl group which is unsubstituted or substituted at one to five sites with a group selected from a halogen atom; a straight chain or branched alkyl group containing 1 to 10 carbon atoms which is unsubstituted or substituted with one or more halogen atoms; a straight chain or branched alkoxyl group containing 1 to 4 carbon atoms which is unsubstituted or substituted with one or more halogen atoms; phenoxy group; and nitro group; and most preferably, phenyl group substituted at one or two sites with a group selected from a halogen atom; a straight chain or branched alkyl group containing 1 to 6 carbon atoms which is substituted with one or more halogen atoms; and a straight chain or branched alkoxyl group containing 1 to 4 carbon atoms which is substituted with one or more halogen atoms.

The substituents Y and Z may preferably be such that Y represents hydrogen atom, and Z represents hydrogen atom, hydroxyl group, acetoxy group, amino group; or that Y and Z together represent hydrazono group which is unsubstituted or independently substituted with one or more members selected from an alkyl group containing 1 to 4 carbon atoms, an alkylidene group containing 2 to 6 carbon atoms, and amidino group; hydroxyimino group which is unsubstituted or substituted with an alkyl group containing 1 to 4 carbon atoms which is unsubstituted or substituted with an alkoxycarbonyl group, or tosyl group; methylene group which is unsubstituted or substituted with cyano group or an aminoalkyl group; or oxygen atom.

The compound represented by formula (IIb'):

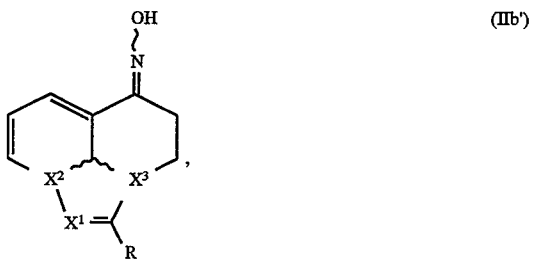

(IIb')

wherein R represents phenyl or naphthyl group which is unsubstituted or substituted at one to five sites with a group optionally selected from a halogen atom; a straight chain or branched alkyl group containing 1 to 10 carbon atoms which is unsubstituted or substituted with one or more halogen atoms; cyano group; carboxyl group; an alkoxycarbonyl group containing 1 to 4 carbon atoms; hydroxyl group; an alkoxyl group containing 1 to 4 carbon atoms which is unsubstituted or substituted with one or more halogen atoms; phenoxy group; tetrazolyl group; amino group which is unsubstituted or substituted at least at one site with a straight chain or branched alkyl group containing 1 to 4 carbon atoms; and nitro group; and $X^1$–$X^2$~C~$X^3$ represents N—C=C—N, which is an intermediate in synthesizing the nitrogen-containing tricyclic compound (I) of the present invention, also has a strong activity similar to that of the compound of formula (I) to inhibit the production of IgE antibody, and accordingly, it may be used for preventing or curing the allergic diseases as described above.

The nitrogen-containing tricyclic compound of the present invention may be produced by the production processes as described below, which may be modified. With regard to the formulae that will be described below, the substituents in formula (I) are as defined above; and unless otherwise noted, the substituents in other formulae are such that, R represents phenyl or naphthyl group which is unsubstituted or substituted at one to five sites with a group optionally selected from a halogen atom; a straight chain or branched alkyl group containing 1 to 10 carbon atoms which is unsubstituted or substituted with one or more halogen atoms; cyano group; carboxyl group; an alkoxycarbonyl group containing 1 to 4 carbon atoms; hydroxyl group; a straight chain or branched alkoxyl group containing 1 to 4 carbon atoms which is unsubstituted or substituted with one or more halogen atoms; phenoxy group; tetrazolyl group; amino group which is unsubstituted or substituted at least at one site with a straight chain or branched alkyl group containing 1 to 4 carbon atoms; and nitro group;

Y represents hydrogen atom; and

Z represents hydrogen atom; hydroxyl group; acetoxy group; amino group which is unsubstituted or substituted with methylthiopropanoyl group, an alkyl group containing 1 to 4 carbon atoms, an aminoalkyl group containing 1 to 4 carbon atoms, hydroxyethylaminoethyl group, an alkoxyoxalyl group containing 1 to 4 carbon atoms, or an alkylidene group containing 2 to 6 carbon atoms; nitro group; or an alkyl group containing 1 to 4 carbon atoms substituted with amino group; or Y and Z together represent hydrazono group which is unsubstituted or substituted at least at one site with an alkyl group containing 1 to 4 carbon atoms, an alkylidene group containing 2 to 6 carbon atoms, an alkoxycarbonyl group containing 1 to 4 carbon atoms, phenyl group, tosyl group, formyl group, carbamoyl group, amidino group, imidazolidinyl group, pyridyl group, or methoxyphenylethylpiperidinylcarbonyl group; hydroxyimino group which is unsubstituted or substituted with an alkyl group containing 1 to 4 carbon atoms which is unsubstituted or substituted with an alkoxycarbonyl group containing 1 to 4 carbon atoms or carboxyl group, tosyl group, or tetrazolylmethyl group; imino group substituted with an unsubstituted or substituted heteromonocyclic group; methylene group which is unsubstituted or substituted with cyano group or an aminoalkyl group containing 1 to 4 carbon atoms; or oxygen atom;

$X^1$–$X^2$~C~$X^3$ represents CH—N—C=C or N—C=C—N; and

X represents a leaving group such as a halogen atom.

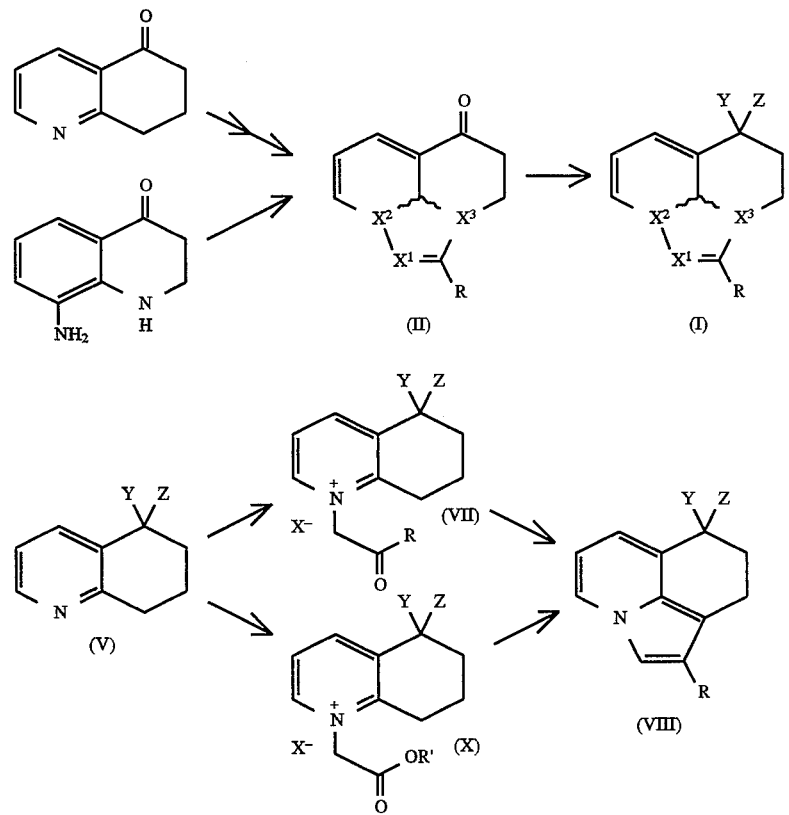

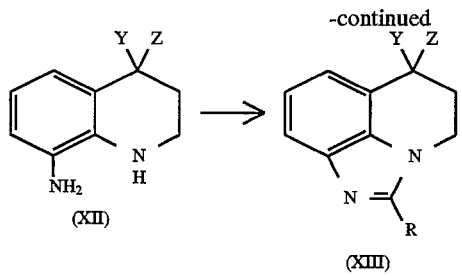

Next, processes for producing the compound of the present invention are schematically shown, and each reaction process is described.

Processes for producing the compound of formula (I)

Production Process A

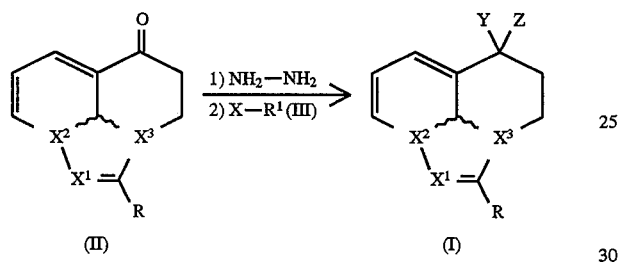

Production Process B

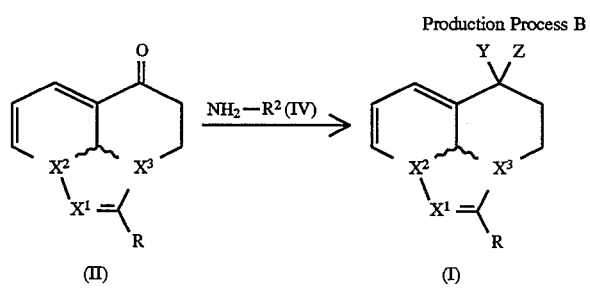

Production Process C

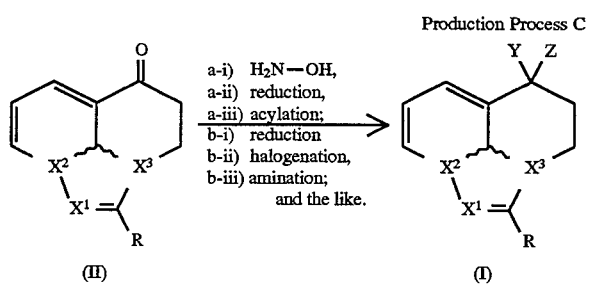

A ketone derivative of formula (II), which is a known compound or may be produced by the processes as will be described later, is reacted with a hydrazine or its salt in an aromatic hydrocarbon solvent; an inert halogenated organic solvent such as dichloromethane or 1,2-dichloroethane; an ethereal solvent such as diethylether or tetrahydrofurane, or dioxane; an alcoholic solvent such as ethanol or methanol; or a mixture of such solvents at a temperature of from −70° C. to the boiling point of the solvent, and preferably, at room temperature to 130° C. to produce a hydrazone represented by formula (IIa):

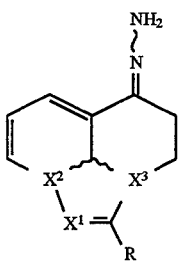

wherein N~N bond represents a syn- or an anti-bond; and R and $X^1$-$X^2$-C-$X^3$ are as defined above for the nitrogen-containing tricyclic compound. Next, the thus produced hydrazone is optionally reacted with a compound represented by formula (III):

R$^1$–X (III)

wherein X represents a leaving group, and R$^1$ represents phenyl group or tosyl group; or with a ketone or aldehyde containing 2 to 6 carbon atoms in the inert solvent as described above at a temperature of from −70° C. to the boiling point of the solvent, and preferably, at room temperature to 130° C. to produce the compound of formula (I). (Production Process A)

Alternatively, the ketone derivative of formula (II) is reacted with a compound represented by formula (IV):

H$_2$N–R$^2$ (IV)

wherein R$^2$ represents amino group unsubstituted or substituted at least one site with an alkyl group containing 1 to 4 carbon atoms, an alkylidene group containing 2 to 6 carbon atoms, phenyl group, tosyl group, formyl group, carbamoyl group, amidino group, imidazolidinyl group, pyridyl group, or methoxyphenylethylpiperidinylcarbonyl group; hydroxyl group which is unsubstituted or substituted with an alkyl group containing 1 to 4 carbon atoms which is unsubstituted or substituted with an alkoxycarbonyl group or carboxyl group, tosyl group, or tetrazolylmethyl group; an unsubstituted or substituted heteromonocyclic group in the inert solvent as described above selected from an aromatic hydrocarbon solvent; an inert halogenated organic solvent such as dichloromethane or 1,2-dichloroethane; an ethereal solvent such as diethylether or tetrahydrofurane, or dioxane; an alcoholic solvent such as ethanol or methanol; and a mixture of such solvents at a temperature of from −70° C. to the boiling point of the solvent, and preferably, at room temperature to 130° C. to produce the compound of formula (I). (Production Process B)

Also, the ketone derivative of formula (II) may be reacted with a hydroxylamine or a its salt in an inert aromatic hydrocarbon solvent; an inert halogenated organic solvent such as dichloromethane or 1,2-dichloroethane; an ethereal solvent such as diethylether or tetrahydrofurane, or dioxane; an alcoholic solvent such as ethanol or methanol; and a mixture of such solvents at a temperature of from −70° C. to the boiling point of the solvent, and preferably, at room temperature to 130° C. to produce the corresponding oxime derivative (IIb):

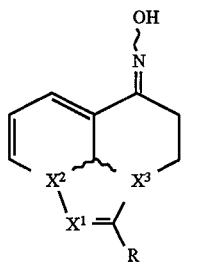

wherein N~O bond represents a syn- or an anti-bond; and R and $X^1$-$X^2$~C~$X^3$ are as defined above.

The resulting oxime derivative may be either hydrogenated in the presence of a metal catalyst such as palladium or reduced by such compound as lithium aluminum hydride to produce an amino derivative (which is a compound of formula (i) wherein Y is hydrogen atom and Z is amino group). If desired, the thus produced amino derivative may be reacted with a methylthiopropanoyl halide, an alkylhalide containing 1 to 4 carbon atoms, or an alkoxyoxalyl halide containing 1 to 4 carbon atoms in the inert solvent as described above such as an aromatic hydrocarbon solvent, a halogenated hydrocarbon solvent, or an ethereal solvent in the presence of a basic catalyst which may typically be a tertiary amine such as triethylamine, pyridine, Dabco, or DBU at a temperature of from −70° C. to the boiling point of the solvent, and preferably, at room temperature to 130° C. to produce the compound of formula (I).

The compound of formula (IIb) may be reacted with a halogenated alkyl containing 1 to 4 carbon atoms which may be substituted or unsubstituted with carboxyl group or with tosyl halide, to modify the oxime group.

Furthermore, the compound of formula (II) may be reacted with ammonium acetate in the above-described inert solvent, in an alcoholic solvent, or in the mixture of such inert solvent and the alcoholic solvent; and the resulting compound may be treated with a reducing reagent such as sodium cyanoborohydride. The resulting compound may be subjected to an optional alkaline hydrolysis to produce an amino derivative.

Still further, the compound of formula (II) may be reacted with an amine derivative of formula (IV'):

$$H_2N-R^{2'} \qquad (IV')$$

wherein $R^{2'}$ represents an alkyl group containing 1 to 4 carbon atoms, an aminoalkyl group containing 1 to 4 carbon atoms, or hydroxyethylaminoethyl group in the inert solvent as described above; and then, the resulting compound may be reduced with a reducing reagent such as sodium borohydride or hydrogenated in the presence of a metal catalyst such as palladium or platinum oxide to produce a compound represented by formula (I) which is a substituted amino derivative.

Still further, the compound of formula (II) may be subjected to an adequate reduction such as reduction with sodium borohydride or Meerwein-Ponndorf reduction to produce a hydroxy derivative. The thus obtained hydroxy derivative may be converted into either a halogeno derivative by using a halogenating reagent such as hydrogen chloride, phosphorus trichloride, phosphorus pentachloride, or phosphorus oxychloride, or a bromate corresponding to such chlorides; or into a sulfonyloxy derivative by using an adequate sulfonylating agent such as mesylchloride or tosylchloride in a halogenated organic solvent such as dichloromethane or in an ethereal solvent such as diethylether, tetrahydrofurane, or dioxane at a temperature of from −70° C. to the boiling point of the solvent, and preferably, at room temperature to 130° C. The resulting hydroxy or sulfonyloxy derivative may be reacted with ammonia or an alkoxyoxalylamine containing 1 to 4 carbon atoms in the inert solvent as described above such as an aromatic hydrocarbon solvent, a halogenated hydrocarbon solvent, or an ethereal solvent in the presence of a basic catalyst which may typically be a tertiary amine such as triethylamine, pyridine, Dabco, or DBU at a temperature of from −70° C. to the boiling point of the solvent, and preferably, at room temperature to 130° C. to produce the compound of formula (I).

Still further, the compound of formula (II) may be reacted with an alkylphosphonium salt containing 1 to 5 carbon atoms which is unsubstituted or substituted with cyano group or amino group; or an alkylphosphate ester corresponding to such an alkylphosphonium salt in an ethereal solvent such as diethylether, tetrahydrofurane, or dioxane in the presence of a base such as potassium hydroxide, potassium t-butoxide or butyllithium at a temperature of from −70° C. to the boiling point of the solvent to produce the compound of formula (I).

Still further, a compound of formula (I) wherein both Y and Z are hydrogen atoms may be produced by further treating the hydrazone derivative produced in accordance with the Production Process A or B with sodium borohydride or heating the hydrazone derivative under alkaline conditions; by subjecting the compound of formula (II) to Clemmensen reduction or thioketal reduction; or by subjecting the above-described halogeno derivative or sulfonyloxy derivative, which is produced by reduction of the ketone group of the compound of formula (II) to hydroxyl group, followed by halogenation or sulfonation, to hydrogenation in the presence of a metal catalyst such as palladium or reduction with such compound as lithium aluminum hydride. (Production Process C)

The compound of formula (I) may be represented by the formula (VIII) when $X^1$-$X^2$~C~$X^3$ is CH—N—C=C. The compound of formula (VIII) may be produced by the processes for the production of the compound of formula (I) as described above, and also, by the processes as described below.

Production Process D

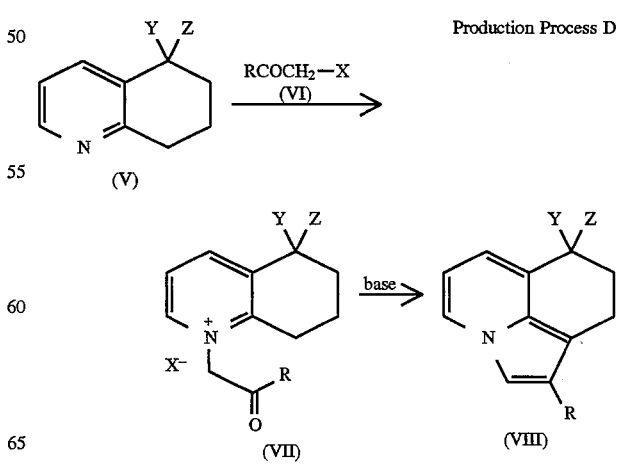

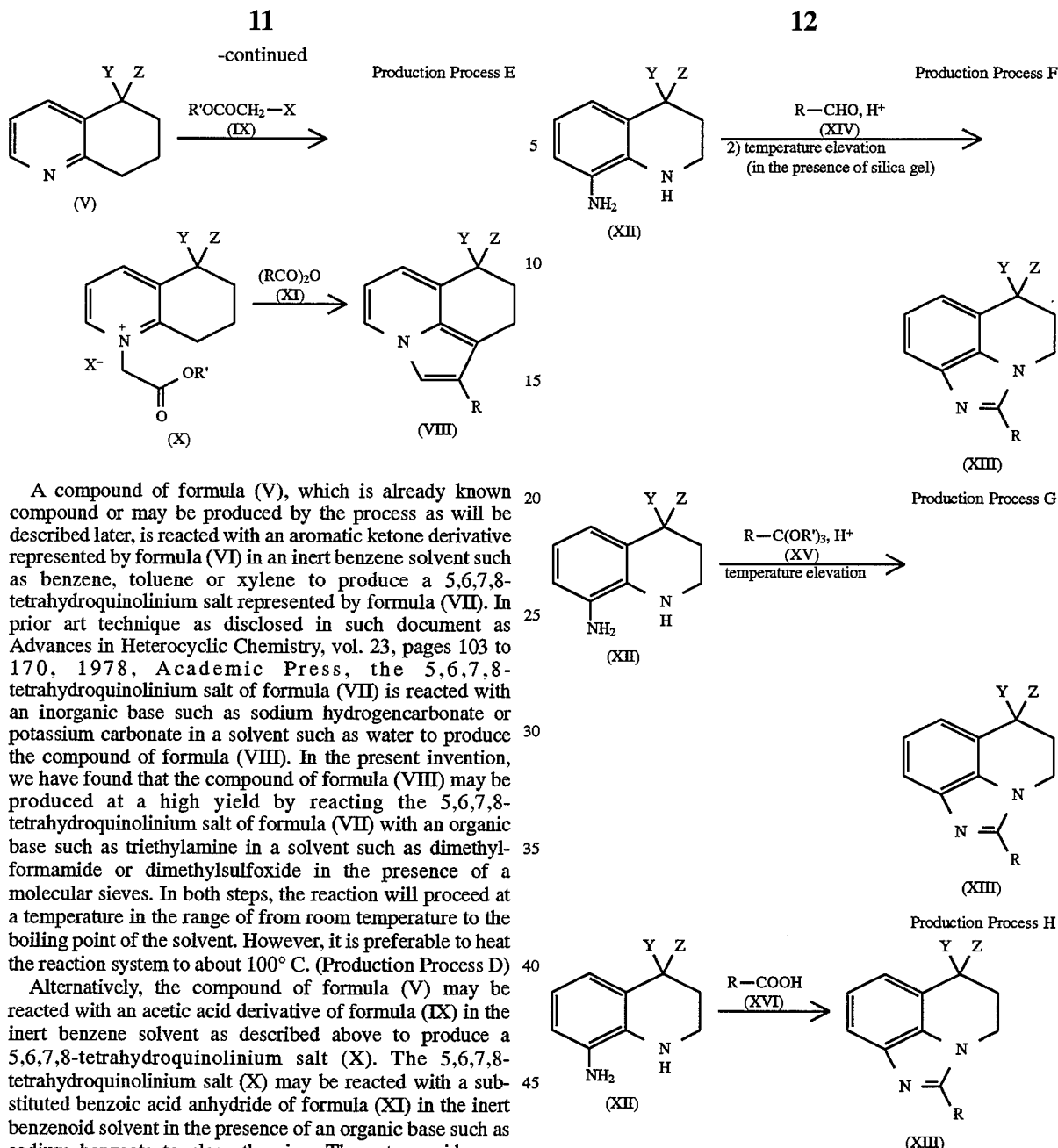

A compound of formula (V), which is already known compound or may be produced by the process as will be described later, is reacted with an aromatic ketone derivative represented by formula (VI) in an inert benzene solvent such as benzene, toluene or xylene to produce a 5,6,7,8-tetrahydroquinolinium salt represented by formula (VII). In prior art technique as disclosed in such document as Advances in Heterocyclic Chemistry, vol. 23, pages 103 to 170, 1978, Academic Press, the 5,6,7,8-tetrahydroquinolinium salt of formula (VII) is reacted with an inorganic base such as sodium hydrogencarbonate or potassium carbonate in a solvent such as water to produce the compound of formula (VIII). In the present invention, we have found that the compound of formula (VIII) may be produced at a high yield by reacting the 5,6,7,8-tetrahydroquinolinium salt of formula (VII) with an organic base such as triethylamine in a solvent such as dimethylformamide or dimethylsulfoxide in the presence of a molecular sieves. In both steps, the reaction will proceed at a temperature in the range of from room temperature to the boiling point of the solvent. However, it is preferable to heat the reaction system to about 100° C. (Production Process D)

Alternatively, the compound of formula (V) may be reacted with an acetic acid derivative of formula (IX) in the inert benzene solvent as described above to produce a 5,6,7,8-tetrahydroquinolinium salt (X). The 5,6,7,8-tetrahydroquinolinium salt (X) may be reacted with a substituted benzoic acid anhydride of formula (XI) in the inert benzenoid solvent in the presence of an organic base such as sodium benzoate to close the ring. The ester residue on second site of the resulting pyrrolo[3,2,1-ij]quinoline is hydrolyzed and decarbonated to produce a compound of formula (VIII). In both steps, the reaction will proceed at a temperature in the range of from room temperature to the boiling point of the solvent. However, it is preferable to heat the reaction system to about 100° C. (Production Process E)

The group X to be eliminated in formula (VI) or (IX) used in Production Process D or E may typically be a halogen atom such as chlorine atom or bromine atom; a sulfate ester such as p-toluenesulfonyloxy group or methanesulfonyloxy group; or phosphate ester, among which the halogen atom being the most preferred in view of operation convenience, reactivity, and the like.

The compound of formula (I) may be represented by the formula (XIII) when $X^1-X^2-C-X^3$ is N—C=C—N. The compound of formula (XIII) may be produced by the processes for the production of the compound of formula (I) as described above, and also, by the processes as described below.

The compound of formula (XII), which is known compound or may be produced by the process as will be described later, is used for the starting material. This compound is reacted with an aldehyde of formula (XIV), an ortho acid ester of formula (XV), or an aromatic carboxylic acid of formula (XVI) to produce the compound of formula (XIII) in accordance with the reaction scheme as shown above. These reactions may be carried out according to the method disclosed in Japanese Patent Application Laid-Open (Kokai) 3(1991)-27382.

In any one of the Production Processes A to H, when the substituent Y, Z, or the substituent on R is a reactive group such as hydroxyl group, amino group, carboxyl group, or hydrazono group, such group may be adequately protected during the reaction process with a protective group, which may be removed at the final stage of the reaction. The method of introducing and removing the protective group may vary in accordance with the type of the group to be protected and the protective group used. Such protection may be carried out, for example, by the process described in T. W. Green, "Protective Groups in Organic Synthesis", 1981, Wiley Company.

The protective groups which may be used to protect the hydroxyl group or the carboxyl group include lower alkyl groups such as methyl group, ethyl group, and t-butyl group; and aralkyl groups such as benzyl group and 4-nitrobenzyl group, among which the lower alkyl group being preferred in view of handling convenience and reactivity. The protective groups which may be used to protect the amino group or the hydrazono group include trityl group, tosyl group, mesyl group, formyl group, chloroacetyl group, and t-butoxycarbonyl group.

Processes for Producing the Compound of Formula (II)

The compound of formula (II) which is an intermediate in the synthesis of the compound of formula (I) may be synthesized by the process as described below.

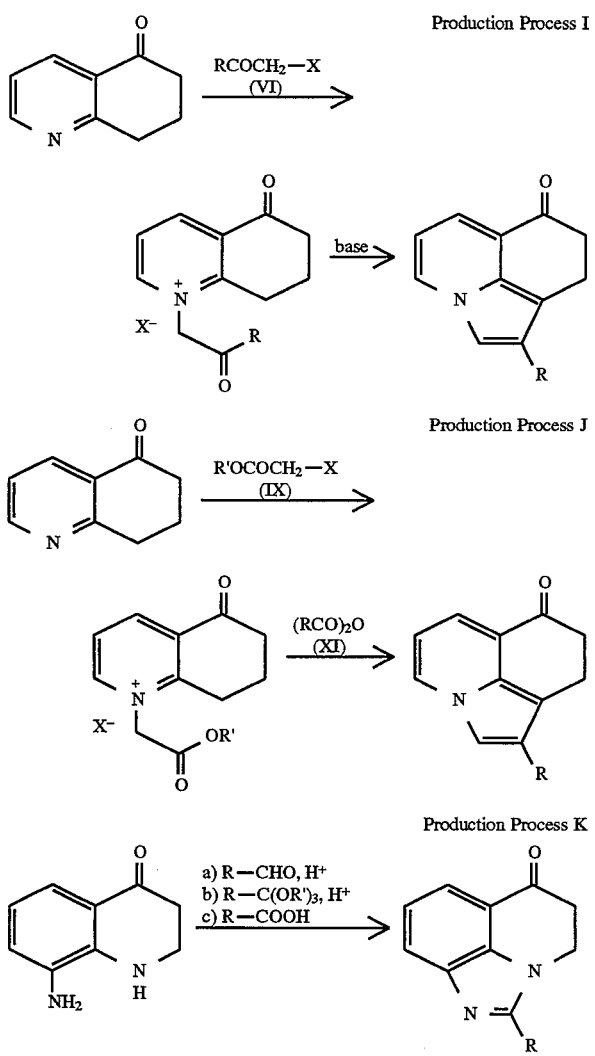

When $X^1$-$X^2$-C-$X^3$ is CH—N—C=C in formula (II), the compound of formula (II) may be produced by using 5,6,7,8-tetrahydroqinolin-5-one, which is a known compound, for the starting material, and subjecting the 5,6,7,8-tetrahydroqinolin-5-one to the reaction process in accordance with the Production Process D or E. (Production Processes I and J)

When $X^1$-$X^2$-C-$X^3$ is N—C=C—N in formula (II), the compound of formula (II) may be produced by using 8-amino-2,3-dihydro-4(1H)-quinolinone, which is a known compound, for the starting material, and subjecting the 8-amino-2,3-dihydro-4(1H)-quinolinone to the reaction process in accordance with any one of the Production Processes F to H. (Production Process K)

The compound of formula (V) and the compound of formula (XII) may be produced by using 5,6,7,8-tetrahydroqinolin-5-one and 8-amino-2,3-dihydro-4(1H)-quinolinone, which are known compounds, respectively, and chemically modifying the ketone group in accordance with the above-described any one of the Production Processes A to C. The amino group of the 8-amino-2,3-dihydro-4(1H)-quinolinone may be preliminarily protected with a protective group for amino group as described above for any one of the Production Processes D to H.

The optical isomer of the compound of formula (I) may be asymmetrically synthesized by a known method. When Y is hydrogen atom, and Z is hydroxyl group, the ketone derivative of formula (II) may be readily converted into an optically active alcohol derivative by the action of an optically active organic boron reagent or a Baker's Yeast. Alternatively, the ketone derivative of formula (II) may be converted into an oxime derivative as described above, and then, converted into an optically active amino derivative, for example, by asymmetrical reduction in the presence a rhodium catalyst. It is also possible to obtain such optically active derivatives by optical resolution according to a known method. These methods of optical isomer production are described in such documents as "Fusei-gosei to kougaku-bunkatsu no shinpo (Progress in asymmetrical synthesis and optical resolution)" (edited by Otsuka and Mukaiyama, 1982, Extra issue of Kagaku, 97, Kagaku-Dojin Shuppan) and "Kou-sentakuteki hannou (Highly selective reactions)" (edited by Nozaki, Mukaiyama and Nozoe, 1981, Extra issue of Kagaku, 91, Kagaku-Dojin Shuppan), and the optical isomers may be produced by referring to such documents.

The therapeutic agent for allergic diseases of the present invention is capable of inhibiting the production of IgE antibody, and accordingly, it may be etiotropically used for the prevention of allergic diseases, prevention of the manifestation of the allergic conditions, prevention of exacerbation of the conditions, and amelioration and cure of the conditions. The allergic diseases that may be prevented or treated by the therapeutic agent of the present invention include allergic diseases mediated by IgE antibody, such as bronchial asthma, hay fever, angioneurotic edema, urticaria, serous tympanitis, atopic dermatitis, pollinosis, allergic rhinitis, allergic gastroenteritis, food allergy, drug allergy, and the like.

Next, pharmacological activity, toxicity, way and dose of the administration, and the like are described with regard to the typical compounds of the present invention by referring to the following experiments.

Experiment 1

Activity to Inhibit the IgE Antibody Production in Mice

Groups of five male BALB/c mice (body weight: 20 to 25 g) each were sensitized by intraperitoneally injection with 4 mg of aluminum hydroxide to which absorbed 10 µg of egg albumin. The test compound is suspended in a gum arabic solution, and the suspensions of different concentrations were orally administered to the animals once a day for seven times in total from immediately after the sensitization. The gum arabic suspension having no test compound added was used for the control.

Blood was collected from the animal ten days after the sensitization, and the collected blood was evaluated for the amount of the IgE antibody produced by ELISA. In brief, the plasma sample was added to immobilized anti-mouse igE antibody, and then, reacting with the anti-mouse IgE antibody having labeled with horseradish peroxidase. The amount of the IgE antibody produced was calculated by using the activity of the horseradish peroxidase for the index (See Meneki-to-Shikkan (Immune and Diseases), 15, 211–216, 1988).

Compounds Tested

Example 3: 1- (4-chlorophenyl) -8,9-dihydro-7H-pyrrolo-[3,2,1-ij]quinoline;

Example 4: 1- (4-bromophenyl) -8,9-dihydro-7H-pyrrolo [3,2,1-ij ]quinolin-7-one hydrazone;

Example 7: 7-amino-1-(4-chlorophenyl)-8,9-dihydro-7H-pyrrolo[3,2,1-ij]quinoline;

Example 9: 1-(4-chlorophenyl)-8,9-dihydro-7-methylene-7H-pyrrolo[3,2,1-ij]quinoline;

Example 15: 2-(4-chlorophenyl)-4,5-dihydro-6H-imidazo-[4,5, 1-ij ]quinolin-6-one hydrazone;

Example 16: 2-(4-chlorophenyl)-4,5-dihydro-6-methoxyimino-6H-imidazo[4,5,1-ij]quinoline;

Example 71: 6-amino-4,5-dihydro-2-(4-trifluoromethylphenyl)-imidazo[4,5,1-ij]quinoline;

Example 81: 8,9-dihydro-1-(4-trifluoromethylphenyl)-7H-pyrrolo[3,2,1-ij]quinolin-7-one;

Example 92: 8,9-dihydro-1-(4-trifluoromethylphenyl)-7H-pyrrolo[3,2,1-ij]quinolin-7-one oxi;

Example 99: 8,9-dihydro-1-(4-fluorophenyl)-7H-pyrrolo-[3,2,1-ij]quinoline;

Example 100: 1-(4-bromophenyl)-8,9-dihydro-7H-pyrrolo-[3,2,1-ij]quinoline;

Example 108: 8,9-dihydro-1- (2-naphthyl)-7H-pyrrolo[3,2,1-ij]quinoline;

Example 109: 8,9-dihydro-1-(4-methylphenyl)-7H-pyrrolo-[3,2,1-ij]quinoline;

Example 117: 1-(4-chlorophenyl)-8,9-dihydro-7H-pyrrolo-[3,2,1-ij]quinolin-7-one hydrazone;

Example 124: 1-(4-chlorophenyl)-8,9-dihydro-7H-pyrrolo-[3,2,1-ij]quinolin-7-one isopropylidenehydrazone;

Example 130: 8,9-dihydro-1-(4-trifluoromethylphenyl)-7H-pyrrolo[3,2,1-ij]quinoline;

Example 132: 7-amino-8,9-dihydro-1-(4-trifluoromethylphenyl)-7H-pyrrolo[3,2,1-ij]quinoline;

Reference Example 30: 2-phenyl-4,5-dihydro-6H-imidazo-[4,5,1-ij]quinolin-6-one oxime;

Reference Example 33: 2-(4-bromophenyl)-4,5-dihydro-6H-imidazo[4,5,1-ij]quinolin-6-one oxime;

Reference Example 34: 2-(4-trifluoromethylphenyl)-4,5-dihydro-6H-imidazo[4,5,1-ij]quinolin-6-one oxime;

Reference Example 36: 2-(2-naphthyl)-4,5-dihydro-6H-imidazo[4,5,1-ij]quinolin-6-one oxime.

In Table 1, there are shown the amount of the test compounds administered and the percentage of the IgE antibody production inhibited calculated by equation 1:

$$\text{Percentage of the IgE antibody production inhibited (\%)} = \left(1 - \frac{\text{Amount of the IgE antibody produced by the test compound}}{\text{Amount of the IgE antibody produced by the control}}\right) \times 100$$

Equation 1

TABLE 1

| Test Compound (Example No.) | Dose (mg/kg/day) | Percentage of the IgE antibody production inhibited (%) |
|---|---|---|
| 3 | 3 | 64 |
| 4 | 30 | 47 |
| 7 | 10 | 49 |
| 9 | 10 | 65 |
| 15 | 30 | 53 |
| 16 | 30 | 54 |
| 71 | 30 | 78 |
| 81 | 30 | 61 |
| 92 | 30 | 50 |
| 99 | 3 | 43 |
| 100 | 10 | 77 |
| 108 | 10 | 71 |
| 109 | 10 | 45 |
| 117 | 30 | 44 |
| 124 | 30 | 45 |
| 130 | 30 | 86 |
| 132 | 30 | 80 |
| (Reference Example No.) | | |
| 30 | 30 | 32 |
| 33 | 30 | 41 |
| 34 | 30 | 32 |
| 36 | 30 | 50 |

All of the compounds of the present invention exhibited significant inhibition of the IgE antibody production in BALB/c mice sensitized by egg albumin.

Experiment 2

Activity to Suppress the Histamine Release

Peritoneal cells were collected from male Wistar rats (9 week-old) killed by exsanguination. The cells were washed by centrifugation, and passively sensitized with rat anti-egg albumin serum. $2\times10^4$ of the sensitized peritoneal cells ($1\times10^4$ of the sensitized peritoneal cells in the case of the compound of Example 12) were reacted with the solution of the test compound (in 0.1% bovine serum albumin solution in HBSS (Hanks' balanced salt solution) containing 0.1% DMSO). Egg albumin was added as allergen, the reaction was allowed to take place for ten minutes. After the cease of the reaction, the amount of the histamine released was determined by post-column fluorometric assay using high-speed liquid chromatography.

The amount of the test compounds administered and the percentage of the histamine release suppressed calculated by equation 2 are shown in Table 2.

Compounds Tested

Example 4: 1-(4-bromophenyl)-8,9-dihydro-7H-pyrrolo [3,2,1-ij]quinolin-7-one hydrazone;

Example 12: 2-(4-chlorophenyl)-4,5-dihydro-6-hydroxy-6H-imidazo[4,5,1-ij]quinoline;

Example 14: 2-(4-chlorophenyl)-4,5-dihydro-6H-imidazo-[4,5,1-ij]quinolin-6-one isopropylidenehydrazone;

Example 15: 2-(4-chlorophenyl)-4,5-dihydro-6H-imidazo-[4,5,1-ij]quinolin-6-one hydrazone;

Example 17: 2-(4-chlorophenyl)-4,5-dihydro-6H-imidazo-[4,5,1-ij]quinolin-6-one phenylhydrazone;

Example 117: 1-(4-chlorophenyl)-8,9-dihydro-7H-pyrrolo-[3,2,1-ij]quinolin-7-one hydrazone;

Example 119: 1-(4-chlorophenyl)-8,9-dihydro-7H-pyrrolo-[3,2,1-ij]quinolin-7-one phenylhydrazone;

Example 122: 1-(4-chlorophenyl)-8,9-dihydro-7-ethoxyoxalylamino-7H-pyrrolo[3,2,1-ij]quinoline;

Example 123: 1-(4-chlorophenyl)-8,9-dihydro-7H-pyrrolo-[3,2,1-ij]quinolin-7-one tosylhydrazone.

$$\text{Percentage of the histamine release suppressed (\%)} = \left(1 - \frac{\text{Amount of the histamine released by the test compound}}{\text{Amount of the histamine released by the control}}\right) \times 100 \quad \text{Equation 2}$$

TABLE 2

| Test Compound (Example No.) | Dose (μg/ml) | Percentage of the histamine release suppressed (%) |
| --- | --- | --- |
| 4 | 10 | 50 |
| 12 | 10 | 49 |
| 14 | 3 | 55 |
| 15 | 1 | 42 |
| 17 | 3 | 40 |
| 117 | 10 | 47 |
| 119 | 3 | 42 |
| 122 | 10 | 98 |
| 123 | 3 | 33 |

All of the compounds were found to suppress the release of the histamine from the passively sensitized rat peritoneal cells.

Experiment 3

Experiments on Acute Toxicity

To groups of three mice each having a body weight of 20 to 30 g were orally administered 1000 mg/kg of the compounds of Examples 15 and 117 of the present invention. The mice were observed for 7 days after the administration, and no mouse was found dead.

The above-described results reveal that the compounds of the present invention are capable of highly inhibiting the IgE antibody production for a prolonged period in experimental animals sensitized with egg albumin. It was also noted that the antibody production-inhibiting activity was highly selective to give little influence to the production of other immunoglobulins. In addition, the compounds of the present invention are in vitro capable of highly suppressing the histamine release by antigen stimulation from the sensitized mast cells. Further the compounds of the present invention exhibit broncho-constriction-suppressing activity in an animal actively sensitized with egg albumin. The compounds of the present invention also have a very low toxicity, and are highly safe. Accordingly, the compounds of the present invention are quite useful as an etiotropical prophylactic and therapeutic agent for various allergic diseases mediated by IgE antibody such as bronchial asthma, conjunctivitis, rhinitis, dermarls, hypersensitivity, and other allergic diseases, and in particular, as a therapeutic agent for bronchial asthma. In the curing or prevention of such allergic diseases, the compounds of the present invention may be simultaneously used with another conventional therapeutic agents for allergic diseases.

The compounds of the present invention can be formulated in the form of a pharmaceutically acceptable salt, for example, a salt with a mineral acid such as hydrochloric acid, hydrobromic acid, phosphoric acid, or sulfuric acid; a salt with an organic acid such as oxalic acid, citric acid, tartaric acid, maleic acid, alginic acid, p-toluenesulfonic acid, or salicylic acid; an inorganic salt with an alkaline or an alkaline earth metal such as sodium, potassium or calcium; a salt with an organic base such as triethylamine or pyridine; and a salt with amino acids such as glutamic acid or aspartic acid.

The compounds of the present invention or salts thereof may be administered alone. However, they may be formulated into a suitable medical preparation by adequately combining with a commonly used suitable carrier or additive such as exipient, binder, lubricant, coloring agent, or flavoring agent; and if desired, with sterilized water, vegetable oil, or other physiologically acceptable solvent or solubilizer such as ethanol, glycerin, propylene glycol, sorbitol or other polyvalent alcohols; and further with emulsifying or suspending agent such as Tween 80 or gum arabic; or the like.

The therapeutic agent of the present invention may generally be administered perorally, but it may be non-orally administered by intravenous, intramuscular, subcutaneous, or intrarectal administration, or by percutaneously or permucosally absorption.

The dose of the therapeutic agent of the present invention may be a dose sufficient to improve the allergic diseases treated, which may differ by the dosage form, way of administration, frequency of the administration per day, seriousness of the conditions, body weight, age, and the like. It is generally desirable to use a dose of 0.1 to 5,000 mg/day, and preferably, a dose of 1 to 500 mg/day.

The dosage form that may be employed include capsule, pill, tablet, granules, grains, powder; as well as internally used solutions such as suspension, emulsion, lemonade, elixir, and syrup; externally applied solutions such as inhalant, aerosol, and embrocation; solutions for eye drop and nasal drop; poultice, ointment, lotion, liniment, epithem, suppository; aqueous and non-aqueous injections; injections in the form of emulsion and suspension; and injections in the form of solid which is to be dissolved, emulsified or suspended upon its use.

EXAMPLES

This invention will be explained in detail with examples and Reference examples below but is not deemed to be limited thereof. IR (infra red absorption) was measured with KBr pellets or thin film (indicated as "neat") and the values were given in $cm^{-1}$. NMR was measured at 90 MHz or 270 MHz (marked with *) of nuclear magnetic resonance at ambient temperature and the values were given in ppm from TMS (tetramethylsilane) as internal standard. As the solvents, $CDCl_3$ means deuteriated chloroform and DMSO-$d_6$ means deuteriated dimethyl sulfoxide. A multiplicity of signals is designated as follows, s means singlet, d means doublet, t means triplet, q means quartet, dd means doublet of doublet, ddd means doublet of doublet of doublet, tt means triplet of triplet, m means multiplet, brs means broad singlet, and br means broad signal. An integral of signal is expressed in parenthesis.

Reference Example 1

Preparation of 2-(4-chlorophenyl)-4,5-dihydro-6H-imidazo[4,5,1-ij]quinolin-6-one A mixture of 8-amino-2,3-dihydro-4-(1H)-quinolinone (40 g), trimethyl 4-chloroorthobenzoate (58.8 g) and p-toluenesulfonic acid (4.7 g) was refluxed in 400 ml of toluene for 1 hour. The reaction mixture was cooled to the room temperature the brown residue that obtained by concentration of brown reaction mixture under reduced pressure was purified by column chromatography, and the title compound was obtained as colorless needles (45 g).

m.p.: 181.9°–184.6° C.

IR: 1685, 1606, 1465, 1406, 1310, 1281, 1262, 1218, 1093, 1011, 842

NMR (DMSO-$d_6$): 8.0–7.3 m (7H), 4.8 ddd (2H), 3.1 ddd (2H)

Reference Example 2

Preparation of 2-(4-chlorophenyl)-4,5-dihydro-6H-imidazo[4,5,1-ij]quinolin-6-one oxime A mixture of 2-(4-chlorophenyl)-4,5-dihydro-6H-imidazo[4,5,1-ij]quinolin-6-one (10 g), which was obtained in reference example 1, hydroxylamine hydrochloride (5.6 g), and pyridine (6.5 ml) was stirred in 100 ml of ethanol at room temperature for 2 hours. The colorless crystals were collected by filtration and washed with ethanol (200 ml). The title compound was obtained as colorless crystals (10 g).

m.p.: 203.2°–204.6° C.

IR: 3184, 3161, 1600, 1479, 1448, 1099, 1012, 835, 747

NMR (DMSO-$d_6$): 12.0 brs (1H), 8.5–7.4 m (7H), 4.6 t (2H), 3.2 t (2H)

Ketones (Reference examples 3 to 28) listed in Table 3 were prepared according to the production process described in the reference example 1 (Production Process K).

Oximes (Reference examples 29 to 38) listed in Table 4 were prepared according to the production process described in the reference example 2 (Production Process B).

TABLE 3

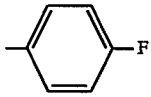

| Reference Example | Y, Z | R | IR KBr | NMR ppm | mp °C. |
|---|---|---|---|---|---|
| 3 | =O | 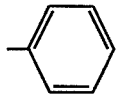 —F | 1689, 1609, 1604, 1465, 1414, 1237, 1164 | DMSO-d6: 8.2–7.8m(3H), 7.7–7.3m(4H), 4.8t(2H), 3.1t(2H) | 153.4–159.0 |
| 4 | =O | 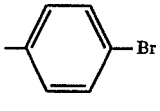 | 1689, 1476, 1444, 1346, 700, 693 | CDCl3: 8.0dd(1H), 7.9–7.5 m(6H), 7.4dd(1H), 4.7t(2H), 3.1t(2H) | 115.3–117.3 |
| 5 | =O | —⟨ ⟩—Br | 1685, 1654, 1606, 1464, 1459, 1349, 1311, 1107 | CDCl3: 8.0d(1H), 7.8–7.5m (5H), 7.4dd(1H), 4.7t(2H), 3.1t(2H) | 183.8–185.4 |
| 6 | =O | 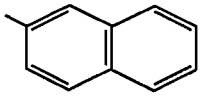 | 1685, 1606, 1497, 1475, 1363, 1347, 1303, 1274, 756 | CDCl3: 8.3s(1H), 8.1–7.5m (8H), 7.4dd(1H), 4.8t(2H), 3.1t(2H) | 144.4–150.5 |
| 7 | =O |  N(C2H5)2 | 1685, 1609, 1465, 1348, 1268, 1198 | CDCl3: 8.0–7.6m(4H), 7.3t (1H), 6.8d(2H), 4.7 t(2H), 3.4q(4H), 3.1t(2H), 1.2t(6H) | 161.7–164.1 |
| 8 | =O | 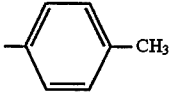 —CH3 | 1682, 1603, 1468, 1342, 1265, 802 | CDCl3: 8.2–7.7m(4H), 7.7–7.2m(3H), 4.7t(2H), 3.1t(2H), 2.5s(3H) | 155.3–162.7 |

TABLE 3-continued
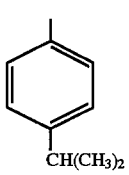
| Reference Example | Y, Z | R | IR KBr | NMR ppm | mp °C. |
|---|---|---|---|---|---|
| 9 | =O | 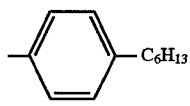 | 2960, 1686, 1601, 1468, 1346, 1282, 1107, 847, 800, 752 | CDCl3: 8.1–7.6m(4H), 7.5–7.2m(3H), 4.7t(2H), 3.2–2.8m(1H), 3.1t(2H), 1.3d(6H) | 101.3–103.1 |
| 10 | =O | 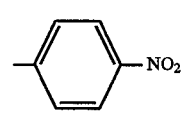 | 2953, 2926, 2854, 1697, 1601, 1464, 1346, 1103, 800, 754 | CDCl3: 8.1–7.6m(4H), 7.5–7.0m(3H), 4.7t(2H), 3.1t(2H), 2.8–2.4m(2H), 2.0–0.8m(11H) | 156.3–160.5 |
| 11 | =O | 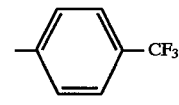 | 1686, 1599, 1520, 1348, 1311, 1107, 710 | DMSO-d6: 8.4d(2H), 8.3d(2H), 8.0d(1H), 7.6d(1H), 7.4t(1H), 4.8t(2H), 3.1t(2H) | 248.2–254.5 |
| 12 | =O | 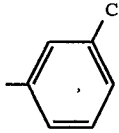 | 1693, 1325, 1174, 1109, 1084, 1066, 752 | CDCl3: 8.1–7.7m(6H), 7.4t(1H), 4.7t(2H), 3.2t(2H) | 134.9–147.3 |
| 13 | =O | 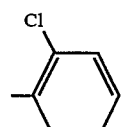 | 1682, 1605, 1477, 1429, 1348, 1309, 1109, 777, 754 | CDCl3: 8.0dd(1H), 7.9–7.2m(6H), 4.7t(2H), 3.1t(2H) | 137.9–139.9 |
| 14 | =O | 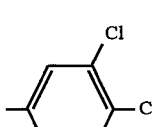 | 1674, 1606, 1479, 1439, 1348, 1311, 779, 748 | CDCl3: 8.0dd(1H), 7.8dd(1H), 7.7–7.4m(4H), 7.4t(1H), 4.5t(2H), 3.1t(2H) | 168.6–171.0 |
| 15 | =O | 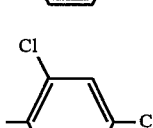 | 1684, 1603, 1450, 1406, 1344, 1308, 1277, 1103 | CDCl3: 8.1–7.8m(2H), 7.8dd(1H), 7.8–7.5m(2H), 7.4t(1H), 4.7t(2H), 3.1t(2H) | 207.4–210.2 |
| 16 | =O | 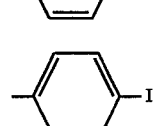 | 1682, 1601, 1471, 1458, 1381, 1348, 1311, 1107, 800 | CDCl3: 8.0dd(1H), 7.8dd(1H), 7.7–7.4m(3H), 7.4t(1H), 4.5t(2H), 3.1t(2H) | 154.0–155.0 |
| 17 | =O |  | 1687, 1603, 1462, 1400, 1346, 1309, 1005, 798, 750 | CDCl3: 8.1–7.8m(3H), 7.8dd(1H), 7.6d(2H), 7.4t(1H), 4.7t(2H), 3.1t(2H) | 75.9–89.2 |

TABLE 3-continued
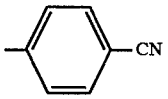
| Reference Example | Y, Z | R | IR KBr | NMR ppm | mp °C. |
|---|---|---|---|---|---|
| 18 | =O | 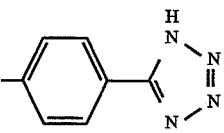 —CN | 2226, 1689, 1605, 1479, 1458, 1412, 1350, 1282, 1107 | CDCl3: 8.1–7.7m(6H), 7.4t (1H), 4.8t(2H), 3.2t (2H) | 148.9–149.8 |
| 19 | =O | 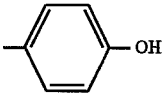 | 3398, 1691, 1605, 1479, 1452, 1350, 1313, 1284, 1109, 854 | DMSO-d6: 8.3s(4H), 8.0d (1H), 7.7d(1H), 7.4 t(1H), 4.9t(2H), 3.1 t(2H) | 180–(dec.) |
| 20 | =O | 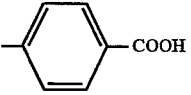 —OH | 1684, 1603, 1475, 1456, 1261 | DMSO-d6: 10.0s(1H), 8.0–7.7 m(3H), 7.5d(1H), 7.3t(1H), 7.0d (2H), 4.7t(2H), 3.1t (2H) | 275.3–278.0 |
| 21 | =O | 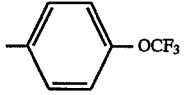 —COOH | 3385, 1689, 1605, 1284, 1238 | DMSO-d6: 8.1s(4H), 8.0d (1H), 7.6d(1H), 7.4 t(1H), 4.8t(2H), 3.1 t(2H) | 250.7–(dec.) |
| 22 | =O | 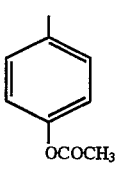 —OCF3 | 1689, 1606, 1464, 1416, 1257, 1207, 1161 | CDCl3: 8.0–7.8m(3H), 7.8 dd(1H), 7.5–7.2m (3H), 4.7t(2H), 3.1t (2H) | 96.7–97.7 |
| 23 | =O | 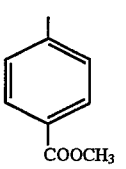 OCOCH3 | 1767, 1686, 1601, 1468, 1414, 1346, 1311, 1194, 1171, 908, 812 | CDCl3: 8.0–7.7m(4H), 7.5–7.2m(3H), 4.7t(2H), 3.1t(2H), 2.3s(3H) | 168.4–170.5 |
| 24 | =O | 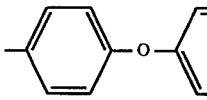 COOCH3 | 1713, 1680, 1606, 1286, 1109 | CDCl3: 8.3–7.7m(6H), 7.4t (1H), 4.8t(2H), 4.0 s(3H), 3.2t(2H) | 198.0–199.2 |
| 25 | =O | 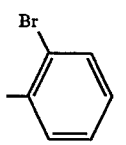 | 1689, 1605, 1585, 1489, 1464, 1242 | CDCl3: 8.1–7.6m(4H), 7.6–6.9m(8H), 4.7t(2H), 3.1t(2H) | 187.8–191.1 |
| 26 | =O | Br | 1676, 1605, 1479, 1441, 1348, 1313, 779, 750 | CDCl3: 8.0dd(1H), 7.9–7.3 m(6H), 4.5t(2H), 3.1t(2H) | 178.0–179.0 |

TABLE 3-continued

[Structure: tetrahydroquinoline with Y,Z at 4-position and N=C(R) substituent at 8-position]

| Reference Example | Y, Z | R | IR KBr | NMR ppm | mp °C. |
|---|---|---|---|---|---|
| 27 | =O | (2-methylphenyl with CF₃) | 1687, 1601, 1479, 1444, 1315, 1128, 777 | CDCl3: 8.1–7.5m(6H), 7.4t (1H), 4.3t(2H), 3.1t (2H) | 145.2–146.1 |
| 28 | =O | (4-methylphenyl with OCH₂CF₂CF₂H) | 1686, 1610, 1477, 1259, 1180, 1117, 1103, 839 | *DMSO-d6: 7.97d(2H), 7.96d (1H), 7.6d(1H), 7.4 t(1H), 7.3d(2H), 6.7tt(1H), 4.8t (2H), 4.7t(2H), 3.1t (2H) | 220.5–221.8 |

TABLE 4

[Structure: tetrahydroquinoline with Y,Z at 4-position and N=C(R) substituent at 8-position]

| Reference Example | Y, Z | R | IR KBr | NMR ppm | mp °C. |
|---|---|---|---|---|---|
| 29 | =NOH | (4-F-phenyl) | 1608, 1493, 1482, 1449, 1165, 1026, 843 | DMSO-d6: 12.0s(1H), 8.3–7.4 m(7H), 4.6t(2H), 3.3 t(2H) | 245.7–250.7 |
| 30 | =NOH | (phenyl) | 1488, 1479, 1455, 1429, 1014, 796, 754, 697 | DMSO-d6: 12.0s(1H), 8.2–7.5 m(8H), 4.7t(2H), 3.3t(2H) | 240.0–243.4 |
| 31 | =NOH | (2-methylphenyl with CF₃) | 3149, 3037, 2843, 1398, 1317, 1174, 1128, 1115, 949 | DMSO-d6: 11.5s(1H), 8.1–7.5 m(6H), 7.3t(1H), 4.1t(2H), 3.1t(2H) | 270.7–(dec.) |
| 32 | =NOH | (2-Br-phenyl) | 3115, 3045, 1595, 1483, 1448, 1358, 1169, 1032 | *DMSO-d6: 11.9s(1H), 8.0–7.6 m(6H), 7.6t(1H), 4.3t(2H), 3.2t(2H) | 272.3–(dec.) |
| 33 | =NOH | (4-Br-phenyl) | 3138, 1597, 1477, 1446, 1022, 748 | *DMSO-d6: 11.9s(1H), 8.0s (4H), 7.83d(1H), 7.76d(1H), 7.6t (1H), 4.6t(2H), 3.2t (2H) | 243.4–245.4 |

TABLE 4-continued

| Reference Example | Y, Z | R | IR KBr | NMR ppm | mp °C. |
|---|---|---|---|---|---|
| 34 | =NOH | —C₆H₄—CF₃ | 3170, 3062, 2873, 1620, 1419, 1325, 1171, 1124 | *DMSO-d6: 11.7s(1H), 8.2d (2H), 8.0d(2H), 7.8d (1H), 7.6d(1H), 7.4 t(1H), 4.6t(2H), 3.2 t(2H) | 232.6–234.1 |
| 35 | =NOH | —C₆H₄—OCF₃ | 3433, 1468, 1421, 1269, 1211, 1174, 949 | *DMSO-d6: 11.5s(1H), 8.1d (2H), 7.7d(1H), 7.6d (2H), 7.5d(1H), 7.3 t(1H), 4.5t(2H), 3.2 t(2H) | 242.2–244.2 |
| 36 | =NOH | naphthyl | 3433, 1626, 1500, 1475, 1394, 1313 | *DMSO-d6: 11.5s(1H), 8.5s (1H), 8.1–8.0m (4H), 7.8–7.5m (4H), 7.3t(1H), 4.7t (2H), 3.2t(2H) | 239.1–241.2 |
| 37 | =NOH | 2-chlorophenyl | 3439, 3161, 1599, 1485, 1439, 1165, 1026 | *DMSO-d6: 11.9s(1H), 7.9–7.6 m(6H), 7.6t(1H), 4.3t(2H), 3.2t(2H) | 290.8–(dec.) |
| 38 | =NOH | —C₆H₄—OCH₂CF₂CF₂H | 3192, 1610, 1493, 1448, 1257, 1186, 1107, 1026 | *DMSO-d6: 12.0s(1H), 8.0d (2H), 7.82d(1H), 7.77d(1H), 7.6t (1H), 7.4d(2H), 6.8 tt(1H), 4.8t(2H), 4.6t(2H), 3.3t(2H) | 194.1–210.6 |

EXAMPLE 1

Preparation of 1-(4-bromophenyl)-8,9-dihydro-7H-pyrrolo[3,2,1-ij]quinolin-7-one 5,6,7,8-Tetrahydroquinolin-5-one (20 g) was dissolved in 500 ml of toluene. To this solution was added 4-bromophenacyl bromide (37.8 g) gradually and refluxed for 18 hours. The reaction mixture was cooled to room temperature, and depositing solids were collected by filtration (33 g). These crystals were dissolved in 300 ml of N,N-dimethylformamide. To this solution was added, molecular sieves 3A (15 g) and triethylamine (13 ml), and the reaction mixture was heated at 100° C. for 1 hour. The reaction mixture became dark brown. The dark brown solution that obtained after removing insoluble matter by filtration was concentrated under reduced pressure. To the residue was added 300 ml of water and extracted with 200 ml of methylene chloride three times. The methylene chloride solution was washed with 100 ml of brine and dried over anhydrous sodium sulfate. The dark brown solution that obtained after removing drying agent by filtration was concentrated under reduced pressure, the resultant dark brown residue was purified by alumina column chromatography. The title compound was obtained as dark brown crystals (12 g).

m.p.: 167.8°–170.4° C.

IR: 1654, 1509, 1382, 1273, 1226, 1101, 1008, 834, 727

NMR (CDCl₃): 8.0 dd (1H), 7.6–7.4 m (5H), 7.1 d (1H), 6.5 t (1H), 3.4 ddd (2H), 3.0 ddd (2H)

EXAMPLE 2

Preparation of 1-(4-chlorophenyl)-8,9-dihydro-7H-pyrrolo[3,2,1-ij]quinolin-7-one 5,6,7,8-Tetrahydroquinolin-5-one (35 g) was dissolved in 80 ml of toluene. To this solution was added 4-chlorophenacyl bromide (55.6 g) gradually and refluxed for 18 hours. The reaction mixture was cooled to room temperature, and depositing crystals were collected by filtration (78 g). These solids were dissolved in 700 ml of N,N-dimethylformamide. To this solution was added, molecular sieves 3A (30 g) and triethylamine (34 ml), then the reaction mixture was heated at 100° C. for 1 hour. The reaction mixture became dark brown. The dark brown solution that obtained after removing insoluble matter by filtration was concentrated under reduced pressure. To the residue was added 300 ml of water, and extracted with 200 ml of methylene chloride three times. This methylene chloride solution was washed with 100 ml of brine and dried over anhydrous sodium sulfate. The dark brown solution that obtained after removing drying agent by filtration was concentrated under reduced pressure, the resultant dark brown residue was purified by alumina column chromatography. The title compound was obtained as dark red crystals (29 g).

m.p.: 153.4°–157.2° C.

IR: 2360, 1683, 1535, 1514, 1471, 1448, 1400, 1384, 1271 264, 1229, 1089, 8365

NMR(CDCl$_3$): 8.0 d (1H), 7.6–7.4 m (5H), 7.1 d (1H), 6.6 t (1H), 3.3 t (2H), 3.0 t (2H)

EXAMPLE 3

Preparation of 1-(4-chlorophenyl)-8,9-dihydro-7H-pyrrolo[3,2,1-ij]quinolin 5,6,7,8-Tetrahydroquinoline (35 g) was dissolved in 500 ml of toluene. To this solution was added 4-chlorophenacyl bromide (61.4 g) gradually and refluxed for 1 hour. The reaction mixture was cooled to room temperature, and depositing crystals were collected by filtration (86 g). These solids were dissolved in 500 ml of N,N-dimethylformamide. To this solution was added, molecular sieves 3A (50 g) and triethylamine (44 ml), then the reaction mixture was heated at 100° C. for 1 hour. The reaction mixture became dark brown. The dark brown solution that obtained after removing insoluble matter by filtration was concentrated under reduced pressure. The resultant brown solids were recrystallized from ethanol (300 ml), and the title compound was obtained as colorless leaflets (50 g).

m.p.: 130.8°–131.1° C.

IR: 2947, 2931, 2917, 2900, 2893, 1515, 1452, 1091, 837, 736

NMR (CDCl$_3$): 7.7–7.2 m (6H), 6.4 dd (1H), 6.3 d (1H), 3.0 t (2H), 2.8 t (2H), 2.0 tt (2H)

EXAMPLE 4

Preparation of 1-(4-bromophenyl)-8,9-dihydro-7H-pyrrolo[3,2,1-ij]quinolin-7-one hydrazone 1-(4-bromophenyl)-8,9-dihydro-7H-pyrrolo[3,2,1-ij] quinolin-7-one (12 g), which was obtained in example 1, was suspended in 100 ml of ethanol. To this suspension was added hydrazine monohydrate (3.6 ml) and stirred at room temperature for 20 hours. The depositing crystals were collected by filtration and washed with 30 ml of ethanol twice. The title compound was obtained as yellow crystals (12 g).

m.p.: 186.5°–189.7° C.

IR: 3194, 3188, 1654, 1637, 1625, 1596, 1533, 1509, 1448, 1440, 1398, 1386, 1290, 1226, 1006, 831, 767, 737, 726

NMR (DMSO-d$_6$): 7.8 d (1H), 7.6–7.3 m (SH), 6.9 d (1H), 6.5 t (1H), 59 brs (2H), 3.2 t (2H), 2.8 t (2H)

EXAMPLE 5

Preparation of 2-(4-chlorophenyl)-4,5-dihydro-6H-imidazo[4,5,1-ij]quinolin-6-one tosylhydrazone A mixture of 2-(4-chlorophenyl)-4,5-dihydro-6H-imidazo [4,5,1-ij]quinolin-6-one (0.5 g), which was obtained in reference example 1, and p-toluenesulfonylhydrazide (0.66 g) was dissolved in 3 ml of ethanol, and stirred at room temperature for 48 hours. The depositing crystals were collected by filtration and washed with ethanol. The title compound was obtained as colorless crystals (0.7 g).

m.p.: 236.8°–237.8° C.

IR: 1464, 1452, 1409, 1374, 1347, 1320, 1183, 1069, 834, 751

NMR (DMSO-d$_6$): 10.8 brs (1H), 8.0–7.1 m (11H), 4.8 t (2H), 3.1 t (2H), 2.4 s (3H)

EXAMPLE 6

Preparation of 6-amino-2-(4-chlorophenyl)-4,5-dihydro-6H-imidazo[4,5,1-ij]quinoline The compound (6 g) obtained in reference example 2 was suspended and hydrogenated in 50 ml of acetic acid and 100 ml of methanol over 10 % Pd/C (0.6 g) at ambient temperature for 8 hours. insoluble matter was filtered off with celite, and the filtrate was concentrated under reduced pressure. To the brown residue was added 100 ml of water and the solution was adjusted to pH 8 with NaHCO$_3$. This solution was extracted with methylene chloride (100 ml×3). This organic solution was washed with brine and dried over anhydrous magnesium sulfate. Removing drying agent by filtration, and solvent by evaporation under reduced pressure of organic solution and afforded brown residue. This brown residue gas purified by column chromatography. The title compound was obtained as brown solid (4.6 g).

m.p.: 141.8°–144.4° C.

IR: 3358, 3030, 2923, 1463, 1365, 1342, 794, 751, 711, 701

NMR (DMSO-d$_6$): 8.0–7.0 m (7H), 4.5 t (2H), 4.2 dd (1H), 2.4–2.0 m (4H)

EXAMPLE 7

Preparation of 7-amino-1-(4-chlorophenyl)-8,9-dihydro-7H-pyrrolo[3,2,1-ij]quinoline 1-(4-chlorophenyl)-8,9-dihydro-7H-pyrrolo[3,2,1-ij] quinolin-7-one (10 g), which was obtained in example 2, was dissolved in 100 ml of CH$_2$Cl$_2$ and 100 ml of methanol at ambient temperature. To this red solution was added ammonium acetate (27.4 g) gradually. After stirring for 3 hours at ambient temperature, to this solution was added NaBH$_3$CN (2.3 g) and stirred for 12 hours at ambient temperature. To this yellow solution was added 500 ml of ethyl acetate and extracted with 3N H$_2$SO$_4$ (20 ml×4) aq. This dil. H$_2$SO$_4$ solution was made alkali with 3N NaOH aq., then yellow crystals were deposited. These crystals were extracted with CH$_2$Cl$_2$ (50 ml×4). This organic layer was washed with brine (30 ml×1) and dried over anhydrous sodium sulfate. Removing drying agent by filtration and solvent by evaporation under reduced pressure of the organic solution afforded yellow residue. This yellow residue was purified by alumina column chromatography, and the title compound was obtained as yellow crystals (6 g).

m.p.: 132.0°–135.0° C.

IR: 3421, 1560, 1517, 1509, 1500, 1092, 832, 735

NMR (CDCl$_3$): 7.7–7.3 m (8H), 6.5–6.4 m (2H), 4.1 dd (2H), 3.1 t (2H), 2.2–1.8 m (2H)

EXAMPLE 8

Preparation of 1-(4-chlorophenyl)-8,9-dihydro-7H-pyrrolo[3,2,1-ij]quinolin-7-one oxime To the solution of 1-(4-chlorophenyl)-8,9-dihydro-7H-pyrrolo[3,2,1-ij]quinolin-7-one (1.93 g), which was obtained in example 2, in 40 ml of ethanol was added hydroxylamine hydrochloride (0.97 g) and pyridine (1.1 ml), then the reaction mixture was stirred for 3 hours at ambient temperature. After condensing the reaction mixture, 100 ml of ethyl acetate was added to the residue, and washed with water and brine, then the organic layer was dried over anhydrous sodium sulfate. After removing drying agent by filtration and solvent by evaporation under reduced pressure, the residue was precipitated with ethyl acetate and ether, and the crystaline title compound was liltrated and given (1.07 g).

m.p.: 203.2°–204.6° C.

IR: 3228, 2927, 2899, 1445, 1012, 935, 869, 765, 732

NMR (DMSO-$d_6$): 11.4 S (1H), 8.1 d (1H), 7.8 S (1H), 7.7–7.4 m (4H), 6.9 d (1H), 6.6 dd (1H), 3.2–2.9 m (4H)

EXAMPLE 9

Preparation of 1-(4-chlorophenyl)-8,9-dihydro-7-methylene-7H-pyrrolo[3,2,1-ij]quinoline Methyltriphenylphosphonium bromide (3.8 g) was added to 25 ml of anhydrous tetrahydrofuran. To this mixture was added the solution of potassium t-butoxide (1.2 g) in 25 ml of tetrahydrofuran at ambient temperature. After stirring for 3 hours, to this solution was added the solution of 1-(4-chlorophenyl)-8,9-dihydro-7H-pyrrolo[3,2,1-ij]quinolin-7-one (1.5 g), which was obtained in example 2, in 15 ml of tetrahydrofuran. After stirring for 30 min., to this solution was added water and extracted with ethyl acetate. The organic solution was washed with brine and dried over anhydrous sodium sulfate. After removing drying agent by filtration and organic solvent by evaporation under reduced pressure, the residue was purified by alumina column chromatography, and the title compound was obtained as yellow crystals (1.1 g) .

m.p.: 125.3°–127.2° C.

IR: 3103, 1513, 1446, 1400, 1093, 833, 741.

NMR (CDCl$_3$): 7.9–7.2 m (6H), 6.7 d (1H), 6.4 t (1H), 5.6 s (1H), 5.2 s (1H), 3.1 t (2H), 2.8 t (2H).

The production processes of compounds in example 1 to 148 are listed in table 5, and the structures, m.p., IR and NMR datum for the compounds in examples 10 to 148 are listed in tables 6 to 9.

TABLE 5

| Production Process | Example No. |
|---|---|
| Process A | 4, 10, 14–15, 19–20, 29–32, 34–47, 50, 117, 120–121, 124 |
| Process B | 5, 8, 13, 16–17, 21–24, 26, 28, 33, 48, 51–53, 59, 64–66, 68, 70, 74, 76, 89–97, 118–119, 123, 125–126, 128–129, 138, 140, 142, 144–147 |
| Process C | 6, 7, 9, 11, 12, 18, 25, 27, 49, 54–58, 60–63, 67, 69, 71–73, 75, 77, 116, 122, 127, 131–137, 139, 141, 143, 148 |
| Process D | 3, 98–115, 130 |
| Process I | 1, 2, 78–88 |

TABLE 6

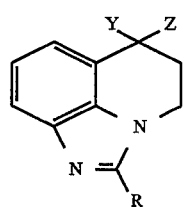

| Example | Y, Z | R | IR KBr | NMR ppm | mp °C. |
|---|---|---|---|---|---|
| 10 | =NNH$_2$ | naphthyl | 3357, 1602, 1475, 1449, 1435, 1390, 1364, 1313, 1266, 825, 795, 753 | CDC13: 8.3s(1H), 8.1–7.4m (8H), 7.3dd(1H), 5.5brs(2H), 4.6t (2H), 3.0t(2H) | 195.6–197.4 |
| 11 | H, H | 4-Cl-phenyl | 1459, 1450, 1426, 1411, 1260, 1100, 840, 784, 749 | CDC13: 7.8d(2H), 7.7–6.9 m(5H), 4.4t(2H), 3.0t(2H), 2.2tt(2H) | 130.1–133.4 |
| 12 | H, OH | 4-Cl-phenyl | 3244, 1464, 1443, 1414, 1115, 1095, 836, 755 | DMSO-d6: 8.0d(2H), 7.7–7.5 m(3H), 7.3–7.1m (2H), 5.5d(1H), 5.0 dt(1H), 4.5t(2H), 2.5m(2H) | 251.5–255.5 |
| 13 | =NOCH$_2$CO$_2$H | 4-Cl-phenyl | 2910, 1718, 1418, 1236, 1224, 1100, 1084, 946, 870 | DMSO-d6: 8.0d(2H), 7.8–7.4 m(4H), 7.3dd(1H), 4.7s(2H), 4.5t (2H), 3.3t(2H) | 237.1–242.7 |

TABLE 6-continued
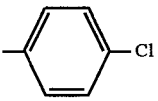
| Example | Y, Z | R | IR KBr | NMR ppm | mp °C. |
|---|---|---|---|---|---|
| 14 | =NNC(CH₃)₂ | 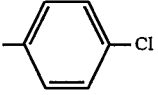 | 1631, 1621, 1474, 1461, 1350, 1305, 1093, 748 | CDCl₃: 7.9–7.7m(4H), 7.6–7.5m(3H), 4.5t (2H), 3.3t(2H), 2.15s(3H), 2.08s (3H) | 151.3–153.5 |
| 15 | =NNH₂ | 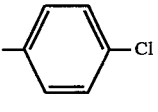 | 3388, 3357, 1462, 1409, 1094, 729, 715 | CDCl₃: 8.0–7.1m(7H), 5.5 brs(2H), 4.5t (2H), 3.0t(2H) | 163.6–167.4 |
| 16 | =NOCH₃ | 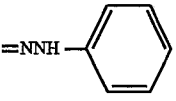 | 1601, 1478, 1446, 1158, 1099, 1045, 1032, 834 | DMSO-d6: 8.2–7.4m(7H), 4.6t (2H), 4.0s(3H), 3.2t(2H) | 177.4–182.0 |
| 17 | =NNH—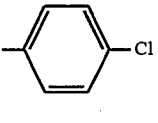 | 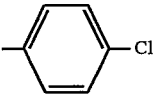 | 3287, 1600, 1577, 1571, 1496, 1474, 1413, 1254, 1163, 751 | DMSO-d6: 9.7brs(1H), 8.1– 6.6m(12H), 4.6t (2H), 3.2t(2H) | 127.1–128.3 |
| 18 | H, NHCOCO₂C₂H₅ | 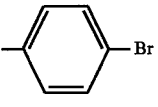 | 1739, 1735, 1700, 1697, 1685, 1542, 1465, 1459, 1412, 1214 | CDCl₃: 7.9–7.1m(8H), 5.6–5.3m(1H), 4.6–4.2m(2H), 4.4 q(2H), 2.6–2.2m (2H), 1.4t(3H) | 213.9–215.6 |
| 19 | =NNH₂ | 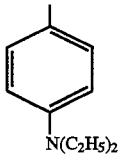 | 3342, 3313, 1459, 1446, 1403, 1364, 1315, 1008, 829, 747 | CDCl₃: 7.9–7.5m(6H), 7.3 t(1H), 5.5brs (2H), 4.5t(2H), 3.0t(2H) | 186.4–187.8 |
| 20 | =NNH₂ | 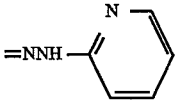 | 3343, 3185, 2967, 1608, 1466, 1430, 1359, 1270, 1198 | CDCl₃: 7.8–7.4m(4H), 7.2 t(1H), 6.7d(2H), 5.5brs(2H), 4.5t (2H), 3.4q(4H), 2.9t(2H), 1.2t(6H) | 165.6–169.4 |
| 21 | =NNH—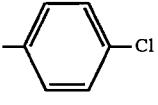 | 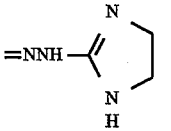 | 1603, 1592, 1577, 1522, 1449, 1438, 1412, 1147, 1092 | DMSO-d6: 10.3brs(1H), 8.2d (1H), 8.0d(2H), 7.8–7.5m(5H), 7.4 d(1H), 7.3 t(1H), 6.8t(1H), 4.6t (2H), 3.3t(2H) | 177.3–180.8 |
| 22 | =NNH—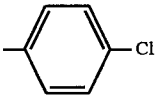 |  | 1659, 1656, 1625, 1608, 1479, 1409, 1377, 1096, 1066, 741 | DMSO-d6: 11.7brs(1H), 8.9– 8.0br(1H), 8.0– 7.5m(6H), 7.3 t (1H), 4.6t(2H), 3.8s(4H), 3.2t (2H) | >300 |

TABLE 6-continued

| Example | Y, Z | R | IR KBr | NMR ppm | mp °C. |
|---|---|---|---|---|---|
| 23 | =NNHCO$_2$C$_2$H$_5$ | 4-Cl-C$_6$H$_4$ | 3221, 2988, 1703, 1529, 1474, 1407, 1251, 1241, 1093, 1051 | DMSO-d6: 10.5s(1H), 8.0d (2H), 7.7–7.4m (4H), 7.3t(1H), 4.5t(2H), 4.2q (2H), 3.1t(2H), 1.3t(3H) | 219.9–(dec.) |
| 24 | =NOCH$_2$-(tetrazol-5-yl) | 4-Cl-C$_6$H$_4$ | 1601, 1477, 1467, 1444, 1419, 1099, 1057, 1014, 839, 797 | DMSO-d6: 8.0d(2H), 7.9–7.6 m(4H), 7.4t(1H), 5.6s(2H), 4.6t (2H), 3.3t(2H) | 285.2–(dec.) |
| 25 | H, NHCOCH$_2$SCH$_3$ | 4-Cl-C$_6$H$_4$ | 3281, 3060, 2910, 1653, 1641, 1542, 1535, 1438, 1409 | DMSO-d6: 7.8d(2H), 7.7d (1H), 7.5d(2H), 7.2 t(1H), 7.1d(1H), 6.6d(1H), 5.5–5.2 m(1H), 4.4t(2H), 3.0–2.5m(4H), 2.4–2.2m(2H), 2.2 s(3H) | 215.4–216.7 |
| 26 | =N-NH-C(=NH)-NH$_2$ | 4-Cl-C$_6$H$_4$ | 3240, 3100, 1674, 1624, 1593, 1463, 1406, 1091 | *DMSO-d6: 11.7brs(1H), 7.9brs (3H), 8.0d(3H), 7.74d(1H), 7.66d (2H), 7.3t(1H), 4.6t(2H), 3.3t(2H) | 284.2–290.4 |
| 27 | =CH$_2$ | 4-Cl-C$_6$H$_4$ | 1460, 1409, 1096, 890, 837, 829, 745 | CDCl3: 7.9–7.2m(7H), 5.7 brs(1H), 5.2brs (1H), 4.4t(2H), 3.0t(2H) | 110.3–111.0 |
| 28 | =N-NH-C(=O)-NH$_2$ | 4-Cl-C$_6$H$_4$ | 3471, 1695, 1577, 1464, 1459, 1408, 1093 | DMSO-d6: 9.8brs(1H), 8.0d (2H), 7.8d(1H), 7.6 d(3H), 7.2t(1H), 6.6brs(2H), 4.5t (2H), 3.1t(2H) | 248.5–250.1 |
| 29 | =NNH$_2$ | 4-F-C$_6$H$_4$ | 3192, 1608, 1470, 1416, 1221, 1157, 849 | CDCl3: 8.0–7.5m(4H), 7.4–7.2m(3H), 5.5brs (2H), 4.5t(2H), 3.0t(2H) | 122.7–127.0 |
| 30 | =NNH$_2$ | 4-CH$_3$-C$_6$H$_4$ | 3398, 3196, 1616, 1471, 1448, 1319, 804, 758 | CDCl3: 7.9–7.5m(4H), 7.4–7.2m(3H), 4.5 t(2H), 3.0t(2H), 2.4s(3H) | 150–(dec.) |
| 31 | =NNH$_2$ | 4-CH(CH$_3$)$_2$-C$_6$H$_4$ | 3194, 2956, 1614, 1468, 1448, 1419, 806, 758 | CDCl3: 7.9–7.6m(4H), 7.5–7.3m(3H), 5.5 brs(2H), 4.5t (2H), 3.1–2.8m (1H), 3.0t(2H), 1.3d(6H) | 176.3–182.1 |

TABLE 6-continued

| Example | Y, Z | R | IR KBr | NMR ppm | mp °C. |
|---|---|---|---|---|---|
| 32 | =NNH₂ | (4-C₆H₁₃-phenyl) | 3396, 3192, 2958, 2927, 2854, 1614, 1466, 1448, 806, 758 | CDCl3: 8.0–7.6m(4H), 7.5–7.2m(3H), 5.5 brs(2H), 4.5t (2H), 3.0t(2H), 2.7t(2H), 2.0–0.7 m(11H) | 156.3–160.5 |
| 33 | =NNHCH₃ | (4-Cl-phenyl) | 2922, 1620, 1606, 1570, 1462, 1406, 1095, 750 | CDCl3: 7.8–7.1m(7H), 5.0 brs(1H), 4.5t (2H), 3.2s(3H), 2.9t(2H) | 118.0–120.7 |
| 34 | =NNH₂ | (4-NO₂-phenyl) | 3336, 3172, 1599, 1518, 1344, 856, 746, 704 | DMSO-d6: 8.4d(2H), 8.2d (2H), 7.7–7.4m (2H), 7.3t(1H), 6.8brs(2H), 4.6t (2H), 3.0t(2H) | 215.0–(dec.) |
| 35 | =NNH₂ | (4-CF₃-phenyl) | 3151, 1618, 1417, 1325, 1120, 1066, 847, 737 | CDCl3: 8.1–7.6m(6H), 7.3t (1H), 5.5brs(2H), 4.5t(2H), 3.0t(2H) | 155.0–(dec.) |
| 36 | =NNH₂ | (3-Cl-phenyl) | 3336, 3186, 1427, 1319, 785, 748, 731, 712 | CDCl3: 7.9–7.2m(7H), 5.5 brs(2H), 4.5t (2H), 3.0t(2H) | 151.9–153.4 |
| 37 | =NNH₂ | (2-Cl-phenyl) | 3392, 3217, 1444, 1392, 770, 750 | CDCl3: 7.8–7.2m(7H), 5.5brs(2H), 4.3t(2H), 3.0t(2H) | 90.7–93.6 |
| 38 | =NNH₂ | (3,4-diCl-phenyl) | 3336, 3209, 1452, 1404, 1317, 797, 750 | CDCl3: 8.0d(1H), 7.9–7.4m(4H), 7.3t(1H), 5.5brs(2H), 4.5t (2H), 3.0t(2H) | 145.2–149.4 |
| 39 | =NNH₂ | (2,4-diCl-phenyl) | 3379, 3223, 1443, 1392, 1321, 825, 804, 744 | CDCl3: 7.8–7.1m(6H), 5.5brs(2H), 4.2t(2H), 3.0t(2H) | 206.2–207.7 |
| 40 | =NNH₂ | (4-I-phenyl) | 3433, 1647, 1630, 1404, 829, 746, 727 | CDCl3: 7.9d(2H), 7.8–7.5m(2H), 7.6d(2H), 7.3dd(1H), 5.5brs (2H), 4.5t(2H), 3.0t(2H) | 260.7–(dec.) |
| 41 | =NNH₂ | (4-tetrazolyl-phenyl) | 3392, 3190, 1616, 1444, 1423, 1350, 748 | DMSO-d6: 8.3–7.1m(7H), 4.6t(2H), 3.0t(2H) | 200–(dec.) |

TABLE 6-continued

| Example | Y, Z | R | IR KBr | NMR ppm | mp °C. |
|---|---|---|---|---|---|
| 42 | =NNH₂ | 4-hydroxyphenyl | 3325, 3219, 1614, 1475, 1390, 1273, 841 | DMSO-d6: 7.8d(2H), 7.5–7.3m(2H), 7.1t(1H), 6.9d(2H), 6.6brs (2H), 4.5t(2H), 2.9t(2H) | 185.3–(dec.) |
| 43 | =NNH₂ | 4-carboxyphenyl | 3371, 3219, 1591, 1547, 1385, 795 | DMSO-d6: 8.1d(2H), 8.0d(2H), 7.6– 7.3m(2H), 7.2t(1H), 6.7brs (2H), 4.5t(2H), 3.0t(2H) | >300 |
| 44 | =NNH₂ | 4-OCF₃-phenyl | 3151, 1614, 1471, 1263, 1213, 1173, 798 | CDCl3: 8.0–7.5m(4H), 7.4–7.1m (3H), 5.5brs(2H), 4.5t(2H), 3.0t(2H) | 140.1–144.4 |
| 45 | =NNH₂ | 4-COOCH₃-phenyl | 3359, 3223, 1705, 1608, 1439, 1410, 1284, 1115, 706 | CDCl3: 8.2d(2H), 8.0d(2H), 7.8– 7.6m(2H), 7.3t(1H), 5.5brs (2H), 4.6t(2H), 4.0s(3H), 3.0t(2H) | 227.0–(dec.) |
| 46 | =NNH₂ | phenyl | 3379, 3205, 1475, 1441, 1387, 777, 743, 710, 700 | CDCl3: 7.8–7.2m(8H), 5.5brs(2H), 4.5t(2H), 3.0t(2H) | 151.3–153.8 |
| 47 | =NNH₂ | 4-phenoxyphenyl | 3413, 3167, 1612, 1587, 1489, 1468, 1230, 752 | CDCl3: 8.0–7.0m(12H), 5.5brs(2H), 4.5t(2H), 3.0t(2H) | 151.0–154.3 |
| 48 | =NN(CH₃)₂ | 4-Cl-phenyl | 2862, 1606, 1464, 1408, 1350, 1315, 1097, 960, 837, 754 | CDCl3: 7.9–7.7m(4H), 7.5d(2H), 7.3t(1H), 4.5t(2H), 3.3t(2H), 2.7s(6H) | 117.7–119.6 |
| 49 | =CHCN | 4-Cl-phenyl | 2206, 1593, 1462, 1410, 1356, 1313, 1092, 791, 746 | CDCl3: 7.9–7.7m(3H), 7.6–7.3m (3H), 7.3t(1H), 6.0brs(1H), 4.5t(2H), 3.3dt(2H) | 185.4–207.0 |
| 50 | H, N=C(CH₃)₂ | 4-Cl-phenyl | 3431, 3059, 2954, 1660, 1458, 1410, 1093, 841, 752 | CDCl3: 8.1–6.8m(7H), 5.0t(1H), 4.8–4.3m(2H), 2.5–2.0m (2H), 2.2s(3H), 2.1s(3H) | 102.7–124.8 |
| 51 | =N–N(piperidinyl) | 4-Cl-phenyl | 2935, 2794, 1462, 1408, 1313, 1095, 839, 746 | CDCl3: 7.9–7.6m(4H), 7.5d(2H), 7.3t(1H),4.5t(2H), 3.3t (2H), 3.0–2.6m(4H), 1.9– 1.3m(6H) | 219.9–221.5 |
| 52 | =N–N(morpholinyl) | 4-Cl-phenyl | 2821, 1610, 1471, 1408, 1309, 1263, 1107, 958, 831 | CDCl3: 7.9–7.6m(4H), 7.5d(2H), 7.3t(1H), 4.5t(2H), 3.9dd (4H), 3.3t(2H), 2.9dd(4H) | 211.0–216.7 |
| 53 | =N–N(imidazolyl) | 4-Cl-phenyl | 1493, 1462, 1408, 1311, 1169, 1097, 1061, 802, 754, 621 | *DMSO-d6: 8.9s(2H), 7.99d(2H), 7.95d (1H), 7.9d(1H), 7.7d(2H), 7.4t(1H), 4.6t(2H), 3.3t(2H) | 229.6–236.0 |

TABLE 6-continued
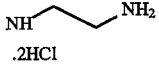
| Example | Y, Z | R | IR KBr | NMR ppm | mp °C. |
|---|---|---|---|---|---|
| 54 | H, -NH-CH₂CH₂-NH₂ .2HCl | 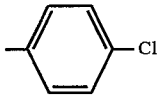 | 3431, 3400, 2958, 1597, 1477, 1446, 1099, 1009, 758 | *DMSO-d6: 10.7brs(1H), 10.4br(1H), 8.4br(3H), 8.0d(2H), 7.9d (1H), 7.8d(2H), 7.7d(1H), 7.6t(1H), 5.1–4.9m(2H), 4.7–4.5m(1H), 3.6–3.2m (3H), 2.9–2.7m(1H), 2.6–2.4m(2H) | 214.9–215.4 |
| 55 | =CHCH₂NH₂.HCl | 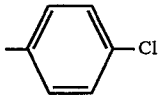 | 3417, 2987, 1616, 1599, 1479, 1448, 1385, 1169, 1095, 791 | *DMSO-d6: 8.6–8.3brs(3H), 8.1d(2H), 7.8d(2H), 7.8d(1H), 7.7d (1H), 7.6t(1H), 6.5t(1H), 4.6t(2H), 3.8–3.7m(2H), 3.1t(2H) | 190.9–192.8 |
| 56 | =CHCH₂NH₂ | 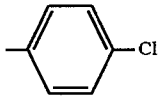 | neat: 3396, 1460, 1441, 1410, 1381, 1371, 1093, 791, 748 | *DMSO-d6: 8.0d(2H), 7.7d(2H), 7.6d (1H), 7.4d(1H), 7.2t(1H), 6.3t(1H), 4.5t(2H), 3.5d (2H), 2.9t(2H) | oil |
| 57 | H, CH₂CH₂NH₂ | 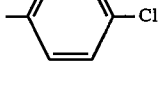 | 3421, 3400, 3030, 3014, 2956, 2929, 1462, 1414, 1385 | *DMSO-d6: 8.0d(2H), 7.8brs(2H), 7.7d (2H), 7.5d(1H), 7.2t(1H), 7.1d(1H), 4.6–4.4m(2H), 3.3–3.2m(1H), 3.1–2.9m (2H), 2.3–1.8m(4H) | 220.0–222.9 |
| 58 | H, NHCH₃.HCl | 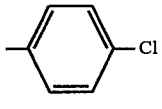 | 3404, 2926, 1470, 1441, 1389, 1342, 750, 698 | DMSO-d6: 8.0brs(2H), 8.1–7.3m(7H), 4.9–4.5m(3H), 2.8–2.4m(5H) | 70.5–75.9 |
| 59 | 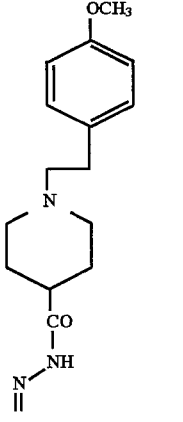 | 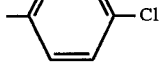 | 2937, 1651, 1512, 1406, 1244, 1093, 746 | CDCl3: 10.1brs(1H), 7.84d(2H), 7.80d(1H), 7.7–7.2m(2H), 7.6s(2H), 7.1d(2H), 6.8d (2H), 4.5t(2H), 3.8s(3H), 3.6–2.9m(5H), 2.9–2.4m (4H), 2.4–1.8m(6H) | 243.0–247.1 |
| 60 | H, CH₂CN | 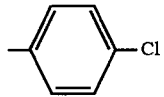 | 2249, 1464, 1441, 1410, 1342, 833, 754 | *CDCl3: 7.8d(2H), 7.7d(1H), 7.5d (2H), 7.3t(1H), 7.1d(1H), 4.5–4.4m(2H), 3.6–3.5m (1H), 3.0dd(1H), 2.7dd (1H), 2.6–2.5m(1H), 2.3–2.2m(1H) | 152.2–153.4 |

TABLE 6-continued

Structure: 4,4-disubstituted (Y, Z) tetrahydroquinoline with N=C-R amidine at position 8.

| Example | Y, Z | R | IR KBr | NMR ppm | mp °C. |
|---|---|---|---|---|---|
| 61 | H, NH₂ | 2-(CF₃)-phenyl | 1437, 1392, 1315, 1167, 1136, 1111, 777 | *CDCl3: 7.9dd(1H), 7.7–7.6m(3H), 7.5dd(1H), 7.3–7.2m(2H), 4.5dd(1H), 4.1–3.9m(2H), 2.7 brs(2H), 2.4–2.1m(2H) | 139.7–142.6 |
| 62 | H, NH–CH₂CH₂–N(H)–CH₂CH₂–OH · 2HCl | 4-Cl-phenyl | 3400, 2956, 2773, 1599, 1479, 1448, 1097, 835, 798, 758 | *DMSO-d6: 10.6brs(1H), 10.4brs(1H), 9.3brs(2H), 8.0d(2H), 7.9d(1H), 7.8d(2H), 7.8–7.7m(1H), 7.6t(1H), 5.0–4.8m(2H), 4.7–4.6m(1H), 4.1brs(1H), 3.7–3.6m(4H), 3.6–3.3m(2H), 3.2–3.0m(2H), 2.9–2.8m(1H), 2.6–2.4m(1H) | 171.5–185.4 |
| 63 | H, NH₂·HCl | 2-Br-phenyl | 3431, 2895, 1601, 1439, 1398, 752 | *DMSO-d6: 8.9brs(3H), 7.9d(1H), 7.7d(1H), 7.6–7.5m(4H), 7.3t(1H), 4.2t(1H), 3.4–3.3m(2H), 2.5–2.3m(2H) | 197.5–206.3 |
| 64 | =NOCH₃ | 2-Br-phenyl | 3433 1477, 1448, 1387, 1319, 1051 | *CDCl3: 7.8d(1H), 7.8–7.7m(2H), 7.6dd(1H), 7.5–7.4m(2H), 7.4t(1H), 4.2t(2H), 4.1s(3H), 3.2t(2H) | 89.3–90.4 |
| 65 | =NOCH₃ | 2-(CF₃)-phenyl | 2939, 1479, 1441, 1387, 1313, 1180, 1130, 1053 | *CDCl3: 7.9–7.5m(6H), 7.4t(1H), 4.1s(3H), 4.0t(2H), 3.2t(2H) | 175.2–177.3 |
| 66 | =NOCH₃ | 4-Br-phenyl | 2935, 1475, 1462, 1406, 1315, 1045, 856 | *DMSO-d6: 7.9d(2H), 7.8d(2H), 7.7d(1H), 7.5d(1H), 7.3t(1H), 4.5t(2H), 4.0s(3H), 3.2t(2H) | 195.7–198.2 |
| 67 | H, NH₂ | 4-Br-phenyl | 3375, 3300, 1460, 1408, 1009, 833, 750 | *CDCl3: 7.8d(2H), 7.7–7.6m(1H), 7.7d(2H), 7.3–7.2m(2H), 4.6–4.4m(3H), 2.4–2.0m(2H), 2.0–1.8br(2H) | 170.3–172.2 |
| 68 | =NOCH₃ | phenyl | 1477, 1443, 1383, 1350, 1057, 928, 856 | *CDCl3: 7.9–7.8m(3H), 7.7d(1H), 7.6–7.5m(3H), 7.3t(1H), 4.5t(2H), 4.1s(3H), 3.3t(2H) | 82.0–83.1 |
| 69 | H, NH₂ | phenyl | 3359, 1468, 1446, 1389, 1365, 1342, 752 | *CDCl3: 7.9–7.8m(2H), 7.7dd(1H), 7.6–7.4m(3H), 7.3–7.2m(2H), 4.6–4.4m(3H), 2.4–2.1m(2H) | 143.6–145.5 |
| 70 | =NOCH₃ | 4-(CF₃)-phenyl | 2947, 1620, 1475, 1416, 1325, 1165, 1124, 1043, 856 | *CDCl3: 8.0d(2H), 7.8–7.7m(4H), 7.7dd(1H), 4.5t(2H), 3.3t(2H) | 140.6–142.1 |

TABLE 6-continued

| Example | Y, Z | R | IR KBr | NMR ppm | mp °C. |
|---|---|---|---|---|---|
| 71 | H, NH$_2$ | 4-CF$_3$-C$_6$H$_4$- | 3433, 1622, 1417, 1327, 1169, 1124 | *CDCl3: 8.0d(2H), 7.8d(2H), 7.7dd (1H), 7.3–7.2m(2H), 4.6– 4.4m(3H), 2.4–2.1m(2H) | 118.3–120.8 |
| 72 | H, NH$_2$ | 4-OCF$_3$-C$_6$H$_4$- | 3431, 1468, 1255, 1215, 1173 | *CDCl3: 7.9d(2H), 7.7–7.6m(1H), 7.4d(2H), 7.3–7.2m(2H), 4.6–4.3m(3H), 2.6brs(2H), 2.4–2.1m(2H) | 98.9–100.8 |
| 73 | H, NH$_2$ | 2-naphthyl | 3431, 1624, 1603, 1500, 1433, 1394, 754 | *CDCl3: 8.3s(1H), 8.0–7.5m(7H), 7.3–7.2m(2H), 4.7–4.4m (3H), 2.4–2.1m(2H) | 159.9–161.8 |
| 74 | =NOCH$_3$ | 4-OCH$_2$CF$_2$CF$_2$H-C$_6$H$_4$- | 1608, 1493, 1450, 1269, 1128, 1107, 1047 | *DMSO-d6: 8.0d(2H), 7.9d(1H), 7.8d (1H), 7.6t(1H), 7.4d(2H), 6.8tt(1H), 4.8t(2H), 4.6t (2H), 4.0s(3H), 3.3t(2H) | 261.3–264.1 |
| 75 | H, NH$_2$ | 4-OCH$_2$CF$_2$CF$_2$H-C$_6$H$_4$- | 3404, 1612, 1462, 1259, 1111, 1093, 837 | *DMSO-d6: 7.9d(2H), 7.5d(1H), 7.3d (2H), 7.22d(1H), 7.15t(1H), 6.7tt(1H), 4.7t(2H), 4.5t (2H), 4.2dd(1H), 2.3– 1.9m(2H) | 102.9–124.3 |
| 76 | =NNHCHO | 4-Cl-C$_6$H$_4$- | 3178, 3066, 1693, 1460, 1406, 1348, 1261, 1095 | DMSO-d6: 11.4d(1H), 8.8d(1H), 8.2– 7.4m(6H), 7.3t(1H), 4.6t (2H), 3.2t(2H) | 210.0–(dec.) |
| 77 | =N-O-SO$_2$-C$_6$H$_4$-4-CH$_3$ | 4-Cl-C$_6$H$_4$- | 1595, 1462, 1406, 1367, 1194, 1178, 1095, 820 | CDCl3: 8.1–7.2m(11H), 4.5t(2H), 3.4t(2H), 2.5s(3H) | 198.7–204.8 |

TABLE 7

| Example | Y, Z | R | IR, KBr | NMR ppm | mp °C. |
|---|---|---|---|---|---|
| 78 | =O | phenyl | 1674, 1538, 1451, 1391, 1103, 767, 713 | DMSO-d6: 8.4d(1H), 7.9s(1H), 7.7–7.3m (5H), 7.0d(1H), 6.6dd(1H), 3.3t(2H), 2.9t(2H) | 125.2–127.1 |
| 79 | =O | 1-naphthyl | 1684, 1671, 1654, 1532, 1449, 1380, 1269, 779 | CDCl3: 8.2–7.7m(4H), 7.6–7.3m(5H), 7.2d (1H), 6.6dd(1H), 3.2–2.7m(4H) | 174.6–176.3 |
| 80 | =O | 2-naphthyl | 1671, 1654, 1625, 1535, 1449, 1388, 1272, 769 | CDCl3: 8.1–7.3m(9H), 7.1d(1H), 6.6dd (1H), 3.5t(2H), 3.0t(2H) | 161.7–164.8 |
| 81 | =O | 4-CF$_3$-phenyl | 3130, 1680, 1616, 1452, 1329, 1240, 1151, 1109, 1072 | *DMSO-d6: 8.4d(1H), 8.1s(1H), 7.84d (2H), 7.78d(2H), 7.0d(1H), 6.7dd(1H), 3.4t(2H), 2.9t(2H) | 130.3–131.7 |
| 82 | =O | 4-NO$_2$-phenyl | 1684, 1595, 1516, 1500, 1335, 1105, 852, 725 | DMSO-d6: 8.4d(1H), 8.3d(2H), 8.1s(1H), 7.9d(2H), 7.0d(1H), 6.7dd(1H), 3.4t(2H), 2.9t(2H) | 216.2–217.0 |
| 83 | =O | 4-OCH$_3$-phenyl | 1686, 1539, 1524, 1385, 1269, 1248, 1186, 833 | DMSO-d6: 8.3d(1H), 7.8s(1H), 7.5d(2H), 6.99d(2H), 6.97d(1H), 6.6dd(1H), 3.8s(3H), 3.3t(2H), 2.9t(2H) | 141.2–142.8 |
| 84 | =O | 2,4-Cl$_2$-phenyl | 1670, 1537, 1512, 1448, 1392, 1273, 1099, 768 | *DMSO-d6: 8.4d(1H), 7.9s(1H), 7.8s(1H), 7.5s(2H), 7.0d(1H), 6.7dd(1H), 3.1t(2H), 2.9t(2H) | 178.9–180.9 |
| 85 | =O | 4-CH$_3$-phenyl | 1680, 1524, 1448, 1385, 1267, 825, 773, 727 | *DMSO-d6: 8.4d(1H), 7.9s(1H), 7.5d(2H), 7.3d(2H), 7.0d(1H), 6.6dd(1H), 3.3t(2H), 2.9t(2H), 2.3s(3H) | 166.2–167.7 |
| 86 | =O | 4-C(CH$_3$)$_3$-phenyl | 2960, 1686, 1537, 1525, 1450, 1387, 1269, 837 | *DMSO-d6: 8.4d(1H), 7.9s(1H), 7.6d(2H), 7.5d(2H), 7.0d(1H), 6.6dd(1H), 3.3t(2H), 2.9t(2H), 1.3s(9H) | 142.7–144.8 |
| 87 | =O | 4-OCF$_3$-phenyl | 1678, 1279, 1261, 1234, 1207, 1149 | *DMSO-d6: 8.4d(1H), 8.0s(1H), 7.8d(2H), 7.5d(2H), 7.0d(1H), 6.7dd(1H), 3.4t(2H), 2.9t(2H) | 111.5–112.1 |
| 88 | =O | 4-OH-phenyl | 3300, 1666, 1525, 1423, 1282, 1267, 1232, 1217, 843 | *DMSO-d6: 9.5s(1H), 8.3d(1H), 7.8s(1H), 7.4d(2H), 7.0d(1H), 6.8d(2H), 6.6dd(1H), 3.3t(2H), 2.9t(2H) | 194.9–196.5 |

TABLE 8

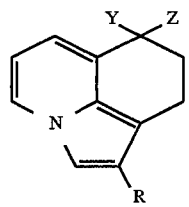

| Example | Y, Z | R | IR, KBr | NMR ppm | mp °C. |
|---|---|---|---|---|---|
| 89 | =NOH | phenyl | 1446, 1391, 1225, 1020, 761, 729, 709 | DMSO-d6: 11.4s(1H), 8.1d(1H), 7.8s(1H), 7.7–7.1m(5H), 6.8d(1H), 6.5dd(1H), 3.3–2.9m(4H) | 192.1–196.4 |
| 90 | =NOH | 4-NO$_2$-phenyl | 3267, 1595, 1504, 1333, 1288, 1111, 851, 717 | DMSO-d6: 11.5s(1H), 8.3d(2H), 8.2d(1H), 8.0s(1H), 7.9d(2H), 6.9d(1H), 6.6dd(1H), 3.2t(2H), 3.0t(2H) | 241.6–243.5 |
| 91 | =NOH | 2,4-dichlorophenyl | 3196, 3124, 1446, 1389, 1018, 937, 874, 764 | *DMSO-d6: 11.5s(1H), 8.2d(1H), 7.7s(2H), 7.5s(2H), 6.9d(1H), 6.6dd(1H), 2.93t(2H), 2.90t(2H) | 188.2–189.8 |
| 92 | =NOH | 4-CF$_3$-phenyl | 3240, 1616, 1329, 1176, 1163, 1122, 1109, 1072 | *DMSO-d6: 11.5s(1H), 8.2d(1H), 8.0s(1H), 7.83d(2H), 7.78d(2H), 6.9d(1H), 6.6dd (1H), 3.2t(2H), 3.0t(2H) | 214.1–215.3 |
| 93 | =NOH | 2-naphthyl | 3230, 3111, 3053, 1446, 1022, 887, 752, 727 | *DMSO-d6: 11.5s(1H), 8.2d(1H), 8.1s(1H), 8.0–7.9m(4H), 7.8d(1H), 7.6–7.4m(2H), 6.9d(1H), 6.6dd(1H), 3.3t(2H), 3.0t(2H) | 199.8–200.6 |
| 94 | =NOH | 4-Br-phenyl | 3230, 1444, 1400, 1018, 1011, 935, 764, 729 | *DMSO-d6: 11.4s(1H), 8.1d(1H), 7.8s(1H), 7.6d(2H), 7.5d(2H), 6.8d(1H), 6.6dd(1H), 3.1t(2H), 3.0t(2H) | 205.6–207.2 |
| 95 | =NOH | 4-OCH$_3$-phenyl | 3219, 3107, 1537, 1443, 1281, 1248, 1178, 1022 | DMSO-d6: 11.4s(1H), 8.1d(1H), 7.7s(1H), 7.5d(2H), 7.0d(2H), 6.8d(1H), 6.5dd(1H), 3.8s(3H), 3.1t(2H), 3.0t(2H) | 192.5–194.7 |
| 96 | =NOH | 4-CH$_3$-phenyl | 3271, 2920, 1450, 1018, 935, 872, 758 | DMSO-d6: 11.4s(1H), 8.1d(1H), 7.8s(1H), 7.5d(2H), 7.2d(2H), 6.8d(1H), 6.5dd(1H), 3.2–2.9m(4H), 2.3s(3H) | 206.1–208.5 |
| 97 | =NOH | 4-OCF$_3$-phenyl | 3230, 2931, 1265, 1230, 1211, 1165 | *DMSO-d6: 11.6s(1H), 8.3d(1H), 8.0s(1H), 7.8d(2H), 7.5d(2H), 7.0d(1H), 6.7dd(1H), 3.2t(2H), 3.1t(2H) | 207.5–208.6 |

TABLE 9

| Example | Y, Z | R | IR KBr | NMR ppm | mp °C. |
|---|---|---|---|---|---|
| 98 | H, H | (phenyl) | 1603, 1450, 1417, 1392, 1223, 1154, 775, 750, 720 | CDCl3: 7.7–7.1m(7H), 6.4–6.2m(2H), 3.1t(2H), 2.8t(2H), 2.0tt(2H) | 117.9–118.9 |
| 99 | H, H | 4-F-phenyl | 2950, 2929, 1526, 1453, 1220, 841, 749, 733 | CDCl3: 7.7–7.4m(3H), 7.3s(1H), 7.2–7.0 m(2H), 6.4–6.2m(2H), 3.0t(2H), 2.8t(2H), 2.0tt(2H) | 114.3–116.5 |
| 100 | H, H | 4-Br-phenyl | 1512, 1450, 1004, 833, 748, 735 | CDCl3: 7.7d(1H), 7.5–7.4m(4H), 7.4s (1H), 6.5–6.2m(2H), 3.0t(2H), 2.8t(2H), 2.0tt(2H) | 131.0–133.8 |
| 101 | H, H | 4-I-phenyl | 2928, 1510, 1450, 1223, 1000, 832, 749, 735 | CDCl3: 7.8–7.6m(3H), 7.4–7.1m(3H), 6.4–6.2m(2H), 3.0t(2H), 2.8t (2H), 2.0tt(2H) | 132.3–139.7 |
| 102 | H, H | 4-NO2-phenyl | 1594, 1517, 1506, 1449, 1328, 1317, 1108, 853, 759 | CDCl3: 8.3d(2H), 7.7–7.6m(3H), 7.5s (1H), 6.5–6.2m(2H), 3.1t(2H), 2.9t(2H), 2.1tt(2H) | 145.5–147.1 |
| 103 | H, H | 4-CN-phenyl | 2223, 1605, 1522, 1447, 1405, 1388, 1178, 843, 761, 754 | CDCl3: 7.8d(1H), 7.7s(4H), 7.4s(1H), 6.5–6.2m(2H), 3.0t(2H), 2.9t (2H), 2.0tt(2H) | 144.5–145.7 |
| 104 | H, H | 4-COOCH3-phenyl | 1709, 1605, 1435, 1283, 1274, 1224, 1180, 1102, 750 | CDCl3: 8.1d(2H), 7.7–7.6m(3H), 7.5s (1H), 6.5–6.2m(2H), 3.9s(3H), 3.1t(2H), 2.8t(2H), 2.1tt(2H) | 118.0–120.2 |
| 105 | H, H | 2,4-diCl-phenyl | 2930, 2916, 1509, 1450, 1440, 1216, 823, 805, 758 | CDCl3: 7.7dd(1H), 7.5dd(1H), 7.4s(1H), 7.4–7.2m(2H), 6.5–6.2m(2H), 2.8t(4H), 2.0tt(2H) | 79.9–80.8 |
| 106 | H, H | 4-OH-phenyl | 2923, 1535, 1527, 1445, 1238, 831, 753 | CDCl3: 7.7d(1H), 7.5d(2H), 7.3s(1H), 6.9d(2H), 6.4–6.2m(2H), 4.9brs (1H), 3.0t(2H), 2.8t(2H), 2.0tt(2H) | 172.6–175.3 |
| 107 | H, H | 4-OCH3-phenyl | 2914, 2831, 1528, 1452, 1248, 1181, 1035, 749 | CDCl3: 7.7d(1H), 7.5d(2H), 7.3s(1H), 6.9d(2H), 6.4–6.1m(2H), 3.8s (3H), 3.0t(2H), 2.8t(2H), 2.0tt(2H) | 103.9–105.2 |
| 108 | H, H | 2-naphthyl | 1654, 1451, 823, 746, 728 | CDCl3: 8.0–7.3m(9H), 6.5–6.2m(2H), 3.2t(2H), 2.9t(2H), 2.1tt(2H) | 141.1–144.2 |

TABLE 9-continued

| Example | Y, Z | R | IR KBr | NMR ppm | mp °C. |
|---|---|---|---|---|---|
| 109 | H, H | 4-CH₃-C₆H₄- | 2921, 2837, 1536, 1450, 1404, 1390, 1302, 1224, 825, 747, 734 | CDCl3: 7.6d(1H), 7.5d(2H), 7.4s(1H), 7.2d(2H), 6.4–6.2m(2H), 3.0t(2H), 2.8t(2H), 2.4s(3H), 2.0tt(2H) | 106.1–107.3 |
| 110 | H, H | 2,4-Cl₂-C₆H₃- | 2922, 2832, 1589, 1446, 1419, 1382, 1099, 1024, 802, 755 | CDCl3: 7.7d(1H), 7.5–7.1m(4H), 6.5–6.2m(2H), 2.9t(4H), 2.0tt(2H) | 109.6–111.5 |
| 111 | H, H | 2-Cl-C₆H₄- | 1446, 1436, 1433, 1418, 1214, 751, 739, 729 | CDCl3: 7.7d(1H), 7.5–7.1m(5H), 6.5–6.2m(2H), 2.9t(4H), 2.0tt(2H), | 115.2–116.2 |
| 112 | H, H | 3-Cl-C₆H₄- | 2938, 1598, 1565, 1561, 1452, 751, 736 | CDCl3: 7.7d(1H), 7.6–7.1m(5H), 6.5–6.2 m(2H), 3.0t(2H), 2.8t(2H), 2.0tt (2H) | 72.3–74.7 |
| 113 | H, H | 2-Br-C₆H₄- | 2929, 1446, 1430, 1418, 1213, 752, 739, 725 | CDCl3: 7.8–7.6m(2H), 7.4–7.0m(4H), 6.5–6.2m(2H), 2.8t(4H), 2.0tt (2H) | 126.1–126.7 |
| 114 | H, H | 3-Br-C₆H₄- | 2931, 2829, 1593, 1558, 1554, 1451, 1407, 750, 736, 715 | CDCl3: 7.8–7.1m(6H), 6.5–6.2m(2H), 3.0t(2H), 2.8t(2H), 2.0tt(2H) | 64.3–70.0 |
| 115 | H, H | 4-COO⁻K⁺-C₆H₄- | 1596, 1588, 1554, 1543, 1533, 1387, 747, 733 | DMSO-d6: 8.0–7.8m(3H), 7.7s(1H), 7.4d (2H), 6.5–6.2m(2H), 2.9t(2H), 2.7t(2H), 1.9tt(2H) | >300 |
| 116 | H, OH | 4-Cl-C₆H₄- | 3345, 3303, 1517, 1452, 1092, 834, 737 | DMSO-d6: 8.0dd(1H), 7.8s(1H), 7.6d(2H), 7.4d(2H), 6.6–6.4m(2H), 4.8dd (1H), 3.0t(2H), 2.3–1.7m(2H) | 170.6–173.8 |
| 117 | =NNH₂ | 4-Cl-C₆H₄- | 1533, 1447, 1440, 1401, 1389, 1289, 1093, 835, 766, 738, 730 | CDCl3: 7.8dd(1H), 7.6–7.3m(4H), 7.4s (1H), 6.9d(1H), 6.5dd(1H), 5.5 brs(2H), 3.2t(2H), 2.8t(2H) | 181.8–182.1 |
| 118 | =NOCH₃ | 4-Cl-C₆H₄- | 1515, 1448, 1401, 1051, 1010, 853, 830, 760 | CDCl3: 7.8dd(1H), 7.6–7.3m(4H), 7.4s (1H), 7.0d(1H), 6.5dd(1H), 4.0s (3H), 3.2–2.9m(4H) | 139.5–141.3 |

TABLE 9-continued

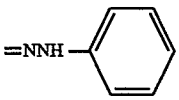

| Example | Y, Z | R | IR KBr | NMR ppm | mp °C. |
|---|---|---|---|---|---|
| 119 | =NNH–C₆H₅ | –C₆H₄–Cl | 1601, 1577, 1571, 1528, 1501, 1474, 1251, 1143, 1091, 752 | CDCl3: 7.8d(1H), 7.6brs(1H), 7.5–7.0m (10H), 7.0–6.7m(1H), 6.5dd (1H), 3.3t(2H), 2.9t(2H) | 156.6–158.4 |
| 120 | =NNH₂ | 1-naphthyl | 1685, 1654, 1648, 1590, 1578, 1381, 804, 778, 758 | CDCl3: 8.0–7.6m(9H), 7.0d(1H), 6.5dd (1H), 5.5brs(2H), 3.1–2.4m(4H) | 110.7–116.3 |
| 121 | =NNH₂ | 2-naphthyl | 3401, 1629, 1625, 1600, 1447, 760 | CDCl3: 8.0–7.3m(9H), 7.0d(1H), 6.5dd (1H), 5.6brs(2H), 3.4t(2H), 2.8t(2H) | 175.7–179.3 |
| 122 | H, NHCOCO₂C₂H₅ | –C₆H₄–Cl | 3238, 1751, 1701, 1686, 1519, 1452, 1205, 736 | CDCl3: 7.8dd(1H), 7.6–7.3m(6H), 6.5–6.3m(2H), 5.5–5.1m(1H), 4.4q (2H), 3.3–3.0m(2H), 2.4–2.0m (2H), 1.4t(3H) | 175.4–176.8 |
| 123 | =N-NH-SO₂-C₆H₄-CH₃ | –C₆H₄–Cl | 3151, 1401, 1390, 1340, 1333, 1316, 1157, 1091, 679 | DMSO-d6: 10.8s(1H), 8.1d(1H), 8.0–7.3m (9H), 6.8d(1H), 6.5dd(1H), 3.3–2.6m(4H), 2.4s(3H) | 205.0–205.9 |
| 124 | =NNC(CH₃)₂ | –C₆H₄–Cl | 2909, 2840, 1627, 1449, 1402, 833, 755, 732 | CDCl3: 7.8d(1H), 7.6–7.1m(6H), 6.5dd (1H), 3.3–2.9m(4H), 2.1s(3H), 2.0s(3H) | 103.8–106.1 |
| 125 | =NOCH₃ | –C₆H₅ | 2926, 1601, 1448, 1390, 1049, 854, 758, 731, 700 | *DMSO-d6: 8.2d(1H), 7.8s(1H), 7.6d(2H), 7.4dd(2H), 7.3t(1H), 6.8d(1H), 66dd(1H), 4.0s(3H), 3.1t(2H), 3.0t(2H) | 82.0–83.9 |
| 126 | =NNHCH₃ | –C₆H₄–Cl | 3259, 1581, 1531, 1444, 1146, 1095, 835, 762, 737, 681 | *DMSO-d6: 8.0d(1H), 7.8s(1H), 7.6d(2H), 7.5d(2H), 6.8d(1H), 6.7brs(1H), 6.5dd(1H), 3.1t(2H), 3.0s(3H), 2.7t(2H) | 179.0–180.1 |
| 127 | H, OCOCH₃ | –C₆H₄–Cl | 1734, 1518, 1454, 1369, 1238, 1090, 1026, 833, 739 | *DMSO-d6: 8.1dd(1H), 7.8s(1H), 7.6d(2H), 7.5d(2H), 6.6–6.5m(2H), 6.0dd (1H), 3.1dd(2H), 2.3–2.0m(2H), 2.1s(3H) | 116.5–118.6 |
| 128 | =NOCH₂CO₂H | –C₆H₄–Cl | 2922, 1738, 1435, 1259, 1095, 993, 870, 766 | *DMSO-d6: 12.8s(1H), 8.2d(1H), 7.9s(1H), 7.6d(2H), 7.5d(2H), 6.8d(1H), 6.6dd(1H), 4.7s(2H), 3.14t(2H), 3.05t(2H) | 201.1–202.0 |

TABLE 9-continued

| Example | Y, Z | R | IR KBr | NMR ppm | mp °C. |
|---|---|---|---|---|---|
| 129 | N—OCH₂COOCH₃ (=N-OCH₂COOCH₃) | 4-Cl-phenyl | 1751, 1514, 1446, 1406, 1209, 1095, 1026, 847, 835 | *DMSO-d6: 8.2d(1H), 7.9s(1H), 7.6d(2H), 7.5d(2H), 6.8d(1H), 6.6dd(1H), 4.8s(2H), 3.7s(3H), 3.15t(2H), 3.05t(2H) | 139.4–140.1 |
| 130 | H, H | 4-CF₃-phenyl | 2935, 1618, 1329, 1161, 1120, 1072, 849, 754 | *DMSO-d6: 8.0d(1H), 7.84s(1H), 7.79d(2H), 7.7d(2H), 6.5dd(1H), 6.3d(1H), 3.0t(2H), 2.8t(2H), 2.0–1.9m(2H) | 119.3–120.0 |
| 131 | H, NH₂ | 4-Br-phenyl | 3406, 3359, 1512, 1448, 1223, 835, 754, 739 | *DMSO-d6: 8.0d(1H), 7.8s(1H), 7.6d(2H), 7.5d(2H), 6.6d(1H), 6.5dd(1H), 4.0dd(1H), 3.0–2.9m(2H), 2.2–2.0m(1H), 1.8–1.7m(1H) | 158.0–159.5 |
| 132 | H, NH₂ | 4-CF₃-phenyl | 3406, 1618, 1333, 1167, 1107, 1072, 851, 764, 741 | *DMSO-d6: 8.0d(1H), 7.9s(1H), 7.8d(2H), 7.7d(2H), 6.6d(1H), 6.5dd(1H), 4.0d(1H), 3.1–3.0m(2H), 2.2–2.1m(1H), 1.9–1.7m(1H) | 149.1–152.4 |
| 133 | H, NH₂ | 4-OCH₃-phenyl | 3367, 1527, 1450, 1248, 1178, 1030, 837, 737 | DMSO-d6: 7.9d(1H), 7.6s(1H), 7.5d(2H), 7.0d(2H), 6.6–6.3m(2H), 4.0dd(1H), 3.8s(3H), 3.3–2.7m(2H), 2.3–1.5m(2H) | 114.5–117.4 |
| 134 | H, NH₂ | 3,4-diCl-phenyl | 3273, 1581, 1552, 1514, 1448, 1373, 1313, 739 | *DMSO-d6: 8.0d(1H), 7.7s(1H), 7.6s(1H), 7.5s(2H), 6.6d(1H), 6.5dd(1H), 4.0dd(1H), 2.9–2.6m(2H), 2.1–2.0m(1H), 1.8–1.7m(1H) | 79.4–81.9 |
| 135 | H, NH₂ | 4-NO₂-phenyl | 3431, 1595, 1497, 1452, 1335, 1109, 852, 729 | *DMSO-d6: 8.3d(2H), 8.01d(1H), 7.96s(1H), 7.9d(2H), 6.6d(1H), 6.5dd(1H), 4.0dd(1H), 3.2–3.0m(2H), 2.2–2.0m(1H), 1.9–1.7m(1H) | 149.1–152.5 |
| 136 | H, NH₂ | phenyl | 3402, 3367, 2931, 1601, 1450, 760, 739, 712 | *DMSO-d6: 8.0d(1H), 7.7s(1H), 7.6d(2H), 7.4dd(2H), 7.2t(1H), 6.6d(1H), 6.5dd(1H), 4.0dd(1H), 3.1–2.9m(2H), 2.2–2.0m(1H), 1.9–1.7m(1H) | 127.5–129.7 |
| 137 | H, NH₂ | 2-naphthyl | 3377, 2918, 1628, 1599, 1448, 858, 822, 756, 739 | *DMSO-d6: 8.1s(1H), 8.0d(1H), 8.0–7.9m(4H), 7.8d(1H), 7.6–7.4m(2H), 6.6d(1H), 6.5dd(1H), 4.1d(1H), 3.3–3.0m(2H), 2.3–2.1m(1H), 2.0–1.8m(1H) | 141.8–143.7 |
| 138 | =NOCH₃ | 4-CF₃-phenyl | 1616, 1323, 1230, 1174, 1163, 1124, 1070, 1057, 841 | *DMSO-d6: 8.2d(1H), 8.0s(1H), 7.81d(2H), 7.77d(2H), 6.9d(1H), 6.6dd(1H), 4.0s(3H), 3.2t(2H), 3.0t(2H) | 117.9–119.5 |

TABLE 9-continued

| Example | Y, Z | R | IR KBr | NMR ppm | mp °C. |
|---|---|---|---|---|---|
| 139 | H, NH₂ | —C₆H₄—CH₃ | 3352, 2916, 1537, 1450, 1379, 825, 762, 735 | *DMSO-d6: 8.0d(1H), 7.7s(1H), 7.5d(2H), 7.2d(2H), 6.54d(1H), 6.46dd (1H), 4.0dd(1H), 3.1–2.9m(2H), 2.3s(3H), 2.2–2.0m(1H), 1.9–1.7m(1H) | 120.5–121.8 |
| 140 | =NOCH₃ | —C₆H₄—NO₂ | 1595, 1504, 1342, 1115, 1043, 860, 849, 756 | DMSO-d6: 8.3d(2H), 8.2d(1H), 8.0s(1H), 7.8d(2H), 6.9d(1H), 6.6dd(1H), 4.0s(3H), 3.3–2.9m(4H) | 158.4–159.0 |
| 141 | H, NH₂ | —C₆H₄—OCH₃ | 3367, 2912, 1578, 1525, 1269, 1209, 1155 | *DMSO-d6: 8.1d(1H), 7.83s(1H), 7.77d(2H), 7.5d(2H), 6.7d(1H), 6.6dd(1H), 4.1–4.0m(1H), 3.2–3.0m(2H), 2.2–2.1m(1H), 2.0–1.8m(1H) | 102.9–106.0 |
| 142 | =NNHCO₂C₂H₅ | —C₆H₄—Cl | 3198, 1724, 1702, 1542, 1533, 1260, 1245, 1092 | DMSO-d6: 10.4s(1H), 8.1d(1H), 7.8s(1H), 7.6d(2H), 7.5d(2H), 6.9d(1H), 6.6t(1H), 4.2q(2H), 3.3–2.7m (4H), 1.3t(3H) | 204.9–206.0 |
| 143 | H, NHCOCH₂CH₂SCH₃ | —C₆H₄—Cl | 3275, 1649, 1541, 1532, 1517, 1451, 1092, 738 | CDCl3: 7.7–7.3m(6H), 6.5–6.4m(2H), 6.0–5.8m(1H), 5.5–5.3m(1H), 3.1–3.0m(2H), 2.9t(2H), 2.5t (2H), 2.2s(3H), 2.2–2.0m(2H) | 200.2–201.7 |
| 144 | =NNH-(2-pyridyl) | —C₆H₄—Cl | 1595, 1574, 1498, 1443, 1138, 1090 | CDCl3: 8.4brs(1H), 8.1d(1H), 7.8d(1H), 7.7–7.1m(8H), 6.9–6.7m(1H), 6.5t(1H), 3.3t(2H), 2.9t(2H) | 161.2–162.7 |
| 145 | =NNH-(4,5-dihydroimidazol-2-yl) | —C₆H₄—Cl | 3136, 1655, 1610, 1402, 1290, 1068, 831 | DMSO-d6: 11.6brs(1H), 8.4brs(1H), 8.2d (1H), 7.9s(1H), 7.6d(2H), 7.5d (2H), 7.3d(1H), 6.6t(1H), 3.8s (4H), 3.3–3.1m(2H), 3.1–2.8m(2H) | 236.4–(dec.) |
| 146 | =N—NH—C(NH₂)=NH | —C₆H₄—Cl | 3392, 3271, 3161, 1673, 1624, 1600, 1126, 1093, 760 | DMSO-d6: 11.7brs(1H), 8.2d(1H), 8.0 brs(3H), 7.9s(1H), 7.6d(2H), 7.5d(2H), 7.4d(1H), 6.6t(1H), 3.3–2.9m(4H) | 229.8–(dec.) |
| 147 | =NOCH₂-(1H-tetrazol-5-yl) | —C₆H₄—Cl | 1404, 1095, 1067, 1040, 1001, 846, 837, 763 | DMSO-d6: 8.2d(1H), 7.8s(1H), 7.6d(2H), 7.4d(2H), 6.9d(1H), 6.5t(1H), 5.6s(2H), 3.2–2.9m(4H) | 193.7–(dec.) |
| 148 | H, OH | —C₆H₄—CF₃ | 3338, 1618, 1329, 1161, 1119, 1072, 845, 741 | *DMSO-d6: 8.1–8.0m(1H), 7.9s(1H), 7.81d (2H), 7.75d(2H), 6.6–6.5m(2H), 5.4d(1H), 4.9–4.7m(1H), 3.1–3.0m(2H), 2.2–1.8m(2H) | 147.2–148.0 |

The following examples detail typical pharmaceutical preparations containing the compound of the present invention, but are not intended to limit this invention.

EXAMPLE A CAPSULES

| compound of Example 3 | 50 g |
|---|---|
| lactose | 935 g |
| magnesium stearate | 15 g |

Above ingredients were weighed and mixed until the mixture become homogeneous. The mixture was then filled in No. 1 hard capsule at 200 mg each to obtain capsule preparation.

EXAMPLE B CAPSULES 50 g of compounds of Example 71 was formulated into capsules in the same manner of example A.

EXAMPLE C TABLETS

| compound of Example 12 | 50 g |
|---|---|
| lactose | 755 g |
| potato starch | 165 g |
| polyvinyl alcohol | 15 g |
| magnesium stearate | 15 g |

After each ingredient was weighed, the compound, lactose and potato starch were mixed to be homogeneous. To this mixture was added polyvinyl alcohol aq. and made into granule by wet granulation. After drying, the granule was mixed with magnesium stearate and formulated into tablets weighing 200 mg each by compression.

EXAMPLE D TABLETS 50 g of compounds of Example 130 was formulated into tablets each weighing 200 mg in the same manner of Example C

INDUSTRIAL UTILITY FIELD

The compound of the present invention is capable of sufficiently inhibiting the production of IgE antibody for a prolonged period, and at the same time, it gives no significant influence on the production of immunoglobulins other than the IgE antibody. In addition, the compound of the present invention has low toxicity. Accordingly, the compound of the present invention may be advantageously used in the prevention of allergic diseases, prevention of the manifestation of the allergic symptoms, prevention of exacerbation of the symptoms, and amelioration and cure of the symptoms. The allergic diseases mediated by IgE antibody that may be treated or prevented by the compound of the present invention include bronchial asthma, conjunctivitis, rhinitis, dermatis, hypersensitivity, and other allergic diseases.

We claim:

1. A nitrogen-containing tricyclic compound represented by formula (I):

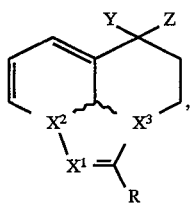

(I)

a salt thereof, or a solvate of said compound or said salt, wherein

R represents phenyl or naphthyl group which is unsubstituted or substituted at one to five sites with a group optionally selected from a halogen atom; a straight chain or branched alkyl group containing 1 to 10 carbon atoms which is unsubstituted or substituted with one or more halogen atoms; cyano group; carboxyl group; an alkoxycarbonyl group containing 1 to 4 carbon atoms; hydroxyl group; a straight chain or branched alkoxyl group containing 1 to 4 carbon atoms which is unsubstituted or substituted with one or more halogen atoms; phenoxy group; tetrazolyl group; amino group which is unsubstituted or substituted at least at one site with a straight chain or branched atkyl group containing 1 to 4 carbon atoms; and nitro group;

Y represents hydrogen atom; and

Z represents hydrogen atom; hydroxyl group; acetoxy group; an amino group which is unsubstituted or substituted with methylthiopropanoyl group, an alkyl group containing 1 to 4 carbon atoms, an aminoalkyl group containing 1 to 4 carbon atoms, a hydroxyethylaminoethyl group, an alkoxyoxalyl group containing 1 to 4 carbon atoms, or an alkylidene group containing 2 to 6 carbon atoms; nitro group; or an alkyl group containing 1 to 4 carbon atoms substituted with amino group; or Y and Z together represent hydrazono group which is unsubstituted or substituted at least at one site with an alkyl group containing 1 to 4 carbon atoms, an alkylidene group containing 2 to 6 carbon atoms, an alkoxycarbonyl group containing 1 to 4 carbon atoms, phenyl group, tosyl group, formyl group, carbamoyl group, amidino group, imidazolidinyl group, pyridyl group, or methoxyphenylethylpiperidinylcarbonyl group; hydroxyimino group which is unsubstituted or substituted with an alkyl group containing 1 to 4 carbon atoms which is unsubstituted or substituted with an alkoxycarbonyl group containing 1 to 4 carbon atoms or carboxyl group, tosyl group, or tetrazolylmethyl group; imino group substituted with an unsubstituted or substituted heteromonocyclic group; methylene group which is unsubstituted or substituted with cyano group or an aminoalkyl group containing 1 to 4 carbon atoms; or oxygen atom; and $X^1$-$X^2$-C-$X^3$ represents CH—N—C=C;

excluding the following both compounds wherein

Y and Z together represent oxygen and R represents unsubstituted phenyl group; and Y and Z represent hydrogen, R represents unsubstituted phenyl group, 4-methoxy phenyl group, 4-bromo phenyl group, and 2-naphthyl group.

2. A compound, a salt thereof, or a solvate of said compound or said salt according to claim 1, wherein said R is phenyl or naphthyl group which is unsubstituted or substituted at one to five sites with a group optionally selected from a halogen atom; a straight chain or branched alkyl group containing 1 to 10 carbon atoms which is unsubstituted or substituted with one or more halogen atoms; a straight chain or branched alkoxyl group containing 1 to 4 carbon atoms which is unsubstituted or substituted with one or more halogen atoms; phenoxy group; and nitro group.

3. A compound, a salt thereof, or a solvate of said compound or said salt according to claim 2, wherein said Y represents hydrogen atom; and Z represents hydrogen atom, hydroxyl group, acetoxy group, or amino group; or Y and Z together represent hydroxyimino group which is unsubstituted or substituted with an alkyl group containing 1 to 4 carbon atoms; methylene group which is unsubstituted or substituted with cyano group or an aminoalkyl group containing 1 to 4 carbon atoms; or oxygen atom.

4. A compound, a salt thereof, or a solvate of said compound or said salt according to claim 3, wherein
   said R is phenyl group substituted at one or two sites with a group optionally selected from a halogen atom; a straight chain or branched alkyl group containing 1 to 4 carbon atoms which is substituted with one or more halogen atoms; and a straight chain or branched alkoxyl group containing 1 to 4 carbon atoms which is substituted with one or more halogen atoms.

5. A prophylactic and/or therapeutic composition for allergic disease comprising an effective amount to treat said allergic disease of a compound represented by formula (I) of claim 1, a salt thereof, or a solvate of said compound or said salt, and a pharmaceutically acceptable carrier.

6. A method for preventing and/or treating an allergic disease, comprising administering to a patient in need of said treatment an effective amount of a compound represented by formula (I) of claim 1, a salt thereof, or a solvate of said compound or said salt.

7. The nitrogen-containing tricyclic compound according to claim 1, wherein R is a phenyl group or naphthyl group that is substituted with a halogen atom; Y is a hydrogen atom; and Z is an amino group.

8. A nitrogen-containing tricyclic compound represented by 7-amino-1-(4-chlorophenyl)-8,9-dihydro-7H-pyrrolo (3,2,1-ij)quinoline.

9. A process for producing a compound represented by formula (I) of claim 1, a salt thereof, or a solvate of said compound or said salt, characterized in that said process comprises
   a) reacting a ketone derivative represented by formula (II):

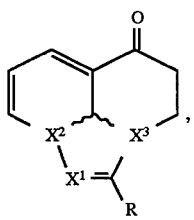

(II)

wherein R represents phenyl or naphthyl group which is unsubstituted or substituted at one to five sites with a group optionally selected from a halogen atom; a straight chain or branched alkyl group containing 1 to 10 carbon atoms which is unsubstituted or substituted with one or more halogen atoms; cyano group; carboxyl group; an alkoxycarbonyl group containing 1 to 4 carbon atoms; hydroxyl group; a straight chain or branched alkoxyl group containing 1 to 4 carbon atoms which is unsubstituted or substituted with one or more halogen atoms; phenoxy group; tetrazolyl group; amino group which is unsubstituted or substituted at least at one site with a straight chain or branched alkyl group containing 1 to 4 carbon atoms; and nitro group; and $X^1$-$X^2$-C-$X^3$ represents CH—N—C=C; with hydrazine or a salt thereof to produce a hydrazone derivative corresponding thereto;
   reacting hydrazono group of said hydrazone derivative with acetone or a compound represented by formula (III):

$R^1$–X (III), wherein X is a leaving group and $R^1$ is phenyl group or tosyl group; and
subjecting the resulting product to an optional reducing treatment;

b) reacting said compound of formula (II) with a compound represented by formula (IV):

$H_2N$–$R^2$ (IV), or a salt thereof, wherein
   $R^2$ is amino group which is unsubstituted or substituted with an alkyl group containing 1 to 4 carbon atoms, an alkylidene group containing 2 to 6 carbon atoms, an alkoxylcarbonyl group containing 1 to 4 carbon atoms, phenyl group, tosyl group, formyl group, carbamoyl group, amidino group, imidazolidinyl group, pyridyl group, or methoxyphenylethylpiperidinylcarbonyl group; hydroxyl group which is unsubstituted or substituted with an alkyl group containing 1 to 4 carbon atoms which is unsubstituted or substituted with an alkoxycarbonyl group containing 1 to 4 carbon atoms or carboxyl group, tosyl group, or tetrazolylmethyl group; or an unsubstituted or substituted heteromonocyclic group; and
   subjecting the resulting product to an optional reducing treatment; or c) treating said compound of formula (II) with a reducing agent to produce a hydroxy derivative; optionally halogenating said hydroxy derivative with a halogenating agent; and aminating the compound to product an amino derivative;
reacting said compound of formula (II) with ammonium acetate; and subjecting the resulting product to a reducing treatment followed by an optional hydrolysis to produce an amino derivative;
reacting said compound of formula (II) with hydroxylamine or its salt to produce an oxime derivative; then reducing said oxime derivative to produce an amino derivative; and optionally reacting said amino derivative with an alkoxyoxalyl halide containing 1 to 4 carbon atoms;
reacting said oxime derivative with an alkyl halide containing 1 to 4 carbon atoms or tosyl halide which is unsubstituted or substituted with carboxyl group to modify the oxime group;
reacting said compound of formula (II) with a compound represented by formula (IV')

$H_2N$–$R^{2'}$ (IV')

wherein $R^2$ is an alkyl group containing 1 to 4 carbon atoms, an aminoalkyl group containing 1 to 4 carbon atoms, or hydroxyethylaminoethyl group; and reducing the resulting compound to produce an amino derivative;
reacting said compound of formula (II) with an alkylphosphonium salt containing 1 to 4 carbon atoms which is unsubstituted or substituted with cyano group or amino group or an alkyl phosphate ester corresponding thereto in the presence of a base such as potassium hydroxide, potassium t-butoxide, or butyllithium; or
reducing ketone group of said compound of formula (II) to hydroxyl group; followed halogenating or sulfonylating the hydroxyl group to produce a halogenated derivative or sulfonyloxy derivative; and reducing said halogenated derivative or said sulfonyloxy derivative.

10. A process for producing a 8,9-dihydro-7H-pyrrolo-[3,2,1-ij]quinoline derivative represented by formula (VIII):

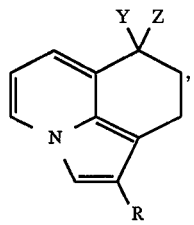
(VIII)

a salt thereof, or a solvate of said derivative or said salt, wherein

R represents phenyl or naphthyl group which is unsubstituted or substituted at one to five sites with a group optionally selected from a halogen atom; a straight chain or branched alkyl group containing 1 to 10 carbon atoms which is unsubstituted or substituted with one or more halogen atoms; cyano group; carboxyl group; an alkoxycarbonyl group containing 1 to 4 carbon atoms; hydroxyl group; a straight chain or branched alkoxyl group containing 1 to 4 carbon atoms which is unsubstituted or substituted with one or more halogen atoms; phenoxy group; tetrazolyl group; amino group which is unsubstituted or substituted at least at one site with a straight chain or branched alkyl group containing 1 to 4 carbon atoms; and nitro group; and Y represents hydrogen atom; and Z represents hydrogen atom; hydroxyl group; acetoxy group; amino group which is unsubstituted or substituted with methylthiopropanoyl group, an alkyl group containing 1 to 4 carbon atoms, an aminoalkyl group containing 1 to 4 carbon atoms, hydroxyethylaminoethyl group, an alkoxyoxalyl group containing 1 to 4 carbon atoms, or an alkylidene group containing 2 to 6 carbon atoms; nitro group; or an alkyl group containing 1 to 4 carbon atoms substituted with amino group; or Y and Z together represent hydrazono group which is unsubstituted or substituted at least at one site with an alkyl group containing 1 to 4 carbon atoms, an alkylidene group containing 2 to 6 carbon atoms, an alkoxycarbonyl group containing 1 to 4 carbon atoms, phenyl group, tosyl group, formyl group, carbamoyl group, amidino group, imidazolidinyl group, pyridyl group, or methoxyphenylethylpiperidinylcarbonyl group; hydroxyimino group which is unsubstituted or substituted with an alkyl group containing 1 to 4 carbon atoms which is unsubstituted or substituted with an alkoxycarbonyl group containing 1 to 4 carbon atoms or carboxyl group, tosyl group, or tetrazolylmethyl group; imino group substituted with an unsubstituted or substituted heteromonocyclic group; methylene group which is unsubstituted or substituted with cyano group or aminoalkyl group containing 1 to 4 carbon atoms; or oxygen atom;

excluding the following compounds wherein:

Y and Z together represent oxygen and R represents unsubstituted phenyl group and Y and Z represent hydrogen, R represents unsubstituted phenyl group, 4-methoxy phenyl group, 4-bromo phenyl group, and 2-phenyl group;

characterized in that said process comprises reacting a 5,6,7,8-tetrahydroquinoline derivative represented by formula (V):

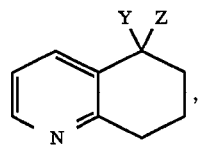
(V)

wherein Y represents hydrogen atom; and

Z represents hydrogen atom; hydroxyl group; acetoxy group; amino group which is unsubstituted or substituted with methylthiopropanoyl group, an alkyl group containing 1 to 4 carbon atoms, an aminoalkyl group containing 1 to 4 carbon atoms, hydroxyethylaminoethyl group, an alkoxyoxalyl group containing 1 to 4 carbon atoms, or an alkylidene group containing 2 to 6 carbon atoms; nitro group; or an alkyl group containing 1 to 4 carbon atoms substituted with amino group; or Y and Z together represent hydrazono group which is unsubstituted or substituted at least at one site with an alkyl group containing 1 to 4 carbon atoms, an alkylidene group containing 2 to 6 carbon atoms, an alkoxycarbonyl group containing 1 to 4 carbon atoms, phenyl group, tosyl group, formyl group, carbamoyl group, amidino group, imidazolidinyl group, pyridyl group, or methoxyphenylethylpiperidinylcarbonyl group; hydroxyimino group which is unsubstituted or substituted with an alkyl group containing 1 to 4 carbon atoms which is unsubstituted or substituted with an alkoxycarbonyl group containing 1 to 4 carbon atoms or carboxyl group, tosyl group, or tetrazolylmethyl group; imino group substituted with an unsubstituted or substituted heteromonocyclic group; methylene group which is unsubstituted or substituted with cyano group or aminoalkyl group containing 1 to 4 carbon atoms; or oxygen atom;

with an aromatic ketone derivative represented by formula (IV):

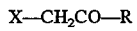
X—CH$_2$CO—R (IV)

wherein X is a leaving group, and R represents phenyl or naphthyl group which is unsubstituted or substituted at one to five sites with a group selected from a halogen atom; a straight chain or branched alkyl group containing 1 to 10 carbon atoms which is unsubstituted or substituted with one or more halogen atoms; cyano group; carboxyl group; an alkoxycarbonyl group containing 1 to 4 carbon atoms; hydroxyl group; a straight chain or branched alkoxyl group containing 1 to 4 carbon atoms which is unsubstituted or substituted with one or more halogen atoms; phenoxy group; tetrazolyl group; amino group which is unsubstituted or substituted at least at one site with a straight chain or branched alkyl group containing 1 to 4 carbon atoms; and nitro group;

to produce a 5,6,7,8-tetrahydroquinolinium salt represented by formula (VII):

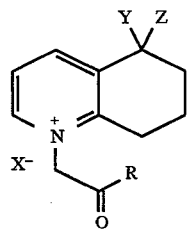
(VII)

wherein X represents a leaving group;

R represents phenyl or naphthyl group which is unsubstituted or substituted at one to five sites with a group optionally selected from a halogen atom; a straight chain or branched alkyl group containing 1 to 10 carbon atoms which is unsubstituted or substituted with one or more halogen atoms; cyano group; carboxyl group; an alkoxycarbonyl group containing 1 to 4 carbon atoms; hydroxyl group; a straight chain or branched chain alkoxyl group containing 1 to 4 carbon atoms which is unsubstituted or substituted with one or more halogen atoms; phenoxy group; tetrazolyl group; amino group which is unsubstituted or substituted at least at one site with a straight chain or branched alkyl group containing 1 to 4 carbon atoms; and nitro group;

Y represents hydrogen atom; and

Z represents hydrogen atom; hydroxyl group; acetoxy group; amino group which is unsubstituted or substituted with methylthiopropanoyl group, an alkyl group containing 1 to 4 carbon atoms, an aminoalkyl group containing 1 to 4 carbon atoms, hydroxyethylaminoethyl group; an alkoxyoxalyl group containing 1 to 4 carbon atoms, or an alkylidene group containing 2 to 6 carbon atoms; nitro group; or an alkyl group containing 1 to 4 carbon atoms substituted with amino group; or Y and Z together represent hydrazono group which is unsubstituted or substituted at least at one site with an alkyl group containing 1 to 4 carbon atoms, an alkylidene group containing 2 to 6 carbon atoms, an alkoxycarbonyl group containing 1 to 4 carbon atoms, phenyl group, tosyl group, formyl group, carbamoyl group, amidino group, imidazolidinyl group, pyridyl group, or methoxyphenylethylpiperidinylcarbonyl group; hydroxyimino group which is unsubstituted or substituted with an alkyl group containing 1 to 4 carbon atoms which is unsubstituted or substituted with an alkoxycarbonyl group containing 1 to 4 carbon atoms or carboxyl group, tosyl group, or tetrazolylmethyl group; imino group substituted with an unsubstituted or substituted heteromonocyclic group; methylene group which is unsubstituted or substituted with cyano group or an aminoalkyl group containing 1 to 4 carbon atoms; or oxygen atom; and reacting said 5,6,7,8-tetrahydroquinolinium salt with a base.

11. A process for producing an 8,9-dihydro-7H-pyrrolo-[3,2,1-ij]quinoline derivative represented by formula (VIII):

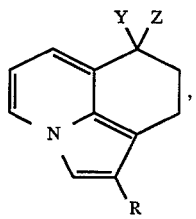 (VIII)

wherein R, Y and Z are as defined for the formula (VIII) in claim 10, characterized in that said process comprises reacting a 5,6,7,8-tetrahydroquinoline derivative represented by formula (V):

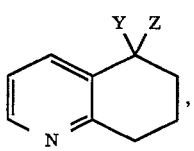 (V)

wherein Y and Z are as defined for the formula (VIII) in claim 10 with an acetic acid derivative represented by formula (IX):

X—CH$_2$COOR'    (IX)

wherein X is a leaving group, and R' represents a protective group for carboxyl group to produce a 5,6,7,8-tetrahydroquinolinium derivative salt represented by formula (X):

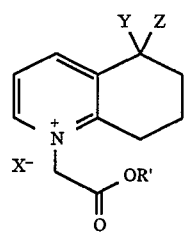 (X)

wherein X represents a group to be eliminated;

Y represents hydrogen atom; and

Z represents hydrogen atom; hydroxyl group; acetoxy group; amino group which is unsubstituted or substituted with methylthiopropanoyl group, an alkyl group containing 1 to 4 carbon atoms, an aminoalkyl group containing 1 to 4 carbon atoms, hydroxyethylaminoethyl group, an alkoxyoxalyl group containing 1 to 4 carbon atoms, or an alkylidene group containing 2 to 6 carbon atoms; nitro group; or an alkyl group containing 1 to 4 carbon atoms substituted with amino group; or Y and Z together represent hydrazono group which is unsubstituted or substituted at least at one site with an alkyl group containing 1 to 4 carbon atoms, an alkylidene group containing 2 to 6 carbon atoms, an alkoxycarbonyl group containing 1 to 4 carbon atoms, phenyl group, tosyl group, formyl group, carbamoyl group, amidino group, imidazolidinyl group, pyridyl group, or methoxyphenylethylpiperidinylcarbonyl group; hydroxyimino group which is unsubstituted or substituted with an alkyl group containing 1 to 4 carbon atoms which is unsubstituted or substituted with an alkoxycarbonyl group containing 1 to 4 carbon atoms or carboxyl group, tosyl group, or tetrazolylmethyl group; imino group substituted with an unsubstituted or substituted heteromonocyclic group; methylene group which is unsubstituted or substituted with cyano group or an aminoalkyl group containing 1 to 4 carbon atoms; or oxygen atom; and R' represents a protective group for carboxyl group;

reacting said 5,6,7,8-tetrahydroquinolinium derivative salt with an acid anhydride represented by formula (XI):

(RCO)$_2$O    (XI)

wherein R is as defined for the formula (VIII) in claim 10; and hydrolyzing the resulting product.

* * * * *